US005597708A

United States Patent [19]

Holder et al.

[11] Patent Number: 5,597,708
[45] Date of Patent: Jan. 28, 1997

[54] CLONING OF A MALARIAL GENE

[75] Inventors: Anthony A. Holder; Michael J. Lockyer; Jasbir S. Sandhu; Valentina Riveros-Moreno, all of Beckenham, England; Karel G. Odink, Rheinfelden, Switzerland

[73] Assignee: Burroughs Wellcome Company, Research Triangle Park, N.C.

[21] Appl. No.: 160,158

[22] Filed: Dec. 2, 1993

Related U.S. Application Data

[63] Continuation of Ser. No. 985,448, Dec. 3, 1992, abandoned, which is a continuation of Ser. No. 678,900, Mar. 28, 1991, abandoned, which is a continuation of Ser. No. 108,273, Oct. 13, 1987, abandoned, which is a division of Ser. No. 703,663, Feb. 21, 1985, abandoned.

[30] Foreign Application Priority Data

Feb. 22, 1984 [GB] United Kingdom .................. 8404692
Sep. 26, 1984 [GB] United Kingdom .................. 8424340

[51] Int. Cl.$^6$ ..................... C12N 15/30; C12N 15/62; C12N 1/21; C12P 21/02
[52] U.S. Cl. ................. 435/69.3; 435/320.1; 435/252.3; 435/254.2; 435/363; 435/325; 435/252.33; 536/23.1; 536/23.4; 536/23.7
[58] Field of Search .................. 435/69.3, 71.1, 435/91, 172.3, 240.2, 252.3, 252.33, 320.1, 235.1, 254.2; 536/27, 23.7, 23.4, 23.1; 530/350; 935/12, 29, 41, 56, 65

[56] References Cited

U.S. PATENT DOCUMENTS 4,466,917  8/1984  Nussenzweig .................... 530/350

OTHER PUBLICATIONS

Young et al Proc. Natl. Acad Sci USA vol. 80 pp. 1194–1198 (1983).
Ellis et al. Nature vol. 302 pp. 536–538 (1983).
Watsai in Molecular Biology of The Gene 3rd Edition W. A. Benjamin Inc. Menlo Park CA (1976) p. 702.
Maniatis et al. Molecular Cloning: A Laboratory Manual Cold Spring Harbor Laboratory CSH, NY (1982) pp. 270–274 or 310–319.
Ada in Fundamental Immunology, 2nd Edition edited by W. E. Paul, Raven Press Ltd, NY (1989) pp. 985–1031.
Butcher Parasitology vol. 98 pp. 315–327 (1989).
Cox TibTech vol. 9 pp. 389–394 (1991).
Eisen in Immunology, 2nd Edition, Harper & Row Publishers, Hagerstown PA (1980) pp. 294 & 436–437.
Stedman's Medical Dictionary 25th Edition Williams & Wilkins Baltimore MD (1990) p. 1680.
Phillips et al Parasitology Today vol. 2 pp. 271–282 (1986).
Nussentweig et al Science vol. 265 pp. 1381–1383 (1994).
Crisanti et al Science vol. 240 pp. 1324–1326 (1988).
Odink et al FEBS vol. 173 pp. 108–112 (Jul. 1984).
Holder et al, "Immunization against *Plasmodium falciparum* with recombinant polypeptides produced in *Escherichia coli*", Parasite Immunology 10:607–617 (1988).
Certa et al, "Aldolase Activity of a *Plasmodium falciparum* Protein with Protective Properties", Science 240:1036–1038 (1988).
Thaithong et al, "Clonal diversity in a single isolate of the malaria parasite *Plasmodium falciparum*", Transactions of the Royal Society of Tropical Medicine and Hygiene, 78:242–245 (1984).
Hall et al, "Major surface antigen genes of a human malaria parasite cloned and expressed in bacteria", Nature 311: (Sep. 1984).
Perrin et al, "Antimalaria Immunity in Saimiri Monkeys", J. Exp. Med. 160:441–451 (1984).
McBride et al, "Serotyping *Plasmodium falciparum* from acute human infections using monoclonal antibodies", Transactions of the Royal Society of Tropical Medicine and Hygiene 78:32–34 (1984).
"Antigenic Diversity in the Human Malaria Parasite", Science 217:254–257 (1982).
Freeman et al, "Surface Antigens of Malaria Merozoites", J. Exp. Med. 158:1647–1653 (1983).
Holder et al, "The Three Major Antigens on the Surface of Plasmodium Falciparum Meroxoites are Derived from a Single High Molecular Weight Precursor", J. Exp. Med. 160:624–629 (1984).
Hall et al, "Processing Polymorphism and Biological Significance of p190, A Major Surface Antigen of the Erythrocytic Forms of *Plasmodium Falciparum*", Molecular and Biochemical Par. 11:61–80 (1984).
Holder et al, "Biosynthesis and Processing of a *Plasmodium Falciparum* Schizont Antigen Recognized by Immune Serum and a Monoclonal Antibody", J. Exp. Med. 156:1528–1538 (1982).
David et al, "Processing of a Major Parasite Surface Glycoprotein During the Ultimate States of Differentiation in *Plasmodium Knowlesi*", Molecular and Biochem. Par. 11:267–282 (1984).
Epstein et al, "Monoclonal Antibodies Against a Specific Surface Determinant on Malarial (*Plasmodium Knowlesi*) Merozoites Block Erythrocyte Invasion", J. of Immunology 127(1):212–217 (1981).
Boyle et al, "Monoclonal Antibodies that Protect In Vivo Against Plasmodium Chabaudi Recognize a 250,000–Dalton Parasite Polypeptide", Infection and Immunity 38(1):94–102 (1982).
Holder et al, "Serological Cross–Reaction Between High Molecular Weight Proteins Synthesized in Blood Schizonts of Plasmodium Yoel II, Plasmodium Chabaudi . . . ", Molecular and Biochem Par. 9;191–196 (1983).
Majarian et al, "Passive Immunization Against Murine Malaria with an IgG3 Monoclonal Antibody", J. of Immunology 32(6):3131–3132 (1984).

(List continued on next page.)

*Primary Examiner*—Mary E. Mosher
*Attorney, Agent, or Firm*—Nixon & Vanderhye P.C.

[57] ABSTRACT

The present invention relates to the P.195 gene of *Plasmodium falciparum* and, more specifically, to the cloning of that gene. The invention further relates to a method of producing the P.195 protein using the cloned gene. The invention also relates to a vaccine comprising the P.195 protein and to the use of same in the prophylaxis of malaria.

16 Claims, 11 Drawing Sheets

OTHER PUBLICATIONS

Freeman et al, "Characteristics of the protective response of BALB/c mice immunized with a purified *Plasmodium yoelii* Schizont antigen", Clin. Exp. Immunol. 54:609–616 (1983).

Laemmli, "Cleavage of Structural Proteins during the Assembly of the Head of Bacteriophage T4", Nature 227:680–685 (1970).

Holder et al, "Characterization of a high molecular weight protective antigen of *Plasmodium yoelii*", Para. 88:211–219 (1984).

Holder et al, "Immunization against blood–stage roden malaria using purified parasite antigens", Nature 294:361–364 (1981).

Odinik et al, Molecular and Biochemical Parasitology, 10:55–66 (1984).

Kemp et al, Proc. Natl. Acad. Sci. USA 30:3787–3791 (1983).

Stites et al, Basic and Clinical Immunology, 5th ed., Lange Medical Publications, Los Allas, CA 1984, p. 698.

Fig. 1A

```
TATATATATA TACATATGTG TAAGGAAAAT AATTTGAATA ATATTAAAAT TATAGTTATG    60

ATGTAATAAA TAATTTTTAT TATAAAAATA AGGCTAATGT AAAATGCAAA AATAAATGTA   120

TACATATTTT TGCTAAGTCA TATTTTTAAA TTATTAACTT ATTTTATTAT TATTATTTTT   180

ATTTATATAT ATTATTTATT AGCTTTAATT CAATA ATG AAG ATC ATA TTC TTT     233
                                       Met Lys Ile Ile Phe Phe
                                         1                   5

TTA TGT TCA TTT CTT TTT TTT ATT ATA AAT ACA CAA TGT GTA ACA CAT    281
Leu Cys Ser Phe Leu Phe Phe Ile Ile Asn Thr Gln Cys Val Thr His
            10                  15                  20

GAA AGT TAT CAA GAA CTT GTC AAA AAA CTA GAA GCT TTA GAA GAT GCA    329
Glu Ser Tyr Gln Glu Leu Val Lys Lys Leu Glu Ala Leu Glu Asp Ala
        25                  30                  35

GTA TTG ACA GGT TAT AGT TTA TTT CAA AAG GAA AAA ATG GTA TTA AAT    377
Val Leu Thr Gly Tyr Ser Leu Phe Gln Lys Glu Lys Met Val Leu Asn
    40                  45                  50

GAA GGA ACA AGT GGA ACA GCT GTT ACA ACT AGT ACA CCT GGT TCA AAG    425
Glu Gly Thr Ser Gly Thr Ala Val Thr Thr Ser Thr Pro Gly Ser Lys
55                  60                  65                  70

GGT TCA GTT GCT TCA GGT GGT TCA GGT GGC TCA GTT GCT TCA GGT GGC    473
Gly Ser Val Ala Ser Gly Gly Ser Gly Gly Ser Val Ala Ser Gly Gly
                75                  80                  85

TCA GTT GCT TCA GGT GGC TCA GTT GCT TCA GGT GGC TCA GTT GCT TCA    521
Ser Val Ala Ser Gly Gly Ser Val Ala Ser Gly Gly Ser Val Ala Ser
                    90                  95                 100

GGT GGT TCA GGT AAT TCA AGA CGT ACA AAT CCT TCA GAT AAT TCA AGT    569
Gly Gly Ser Gly Asn Ser Arg Arg Thr Asn Pro Ser Asp Asn Ser Ser
            105                 110                 115

GAT TCA GAT GCT AAA TCT TAC GCT GAT TTA AAA CAC AGA GTA CGA AAT    617
Asp Ser Asp Ala Lys Ser Tyr Ala Asp Leu Lys His Arg Val Arg Asn
        120                 125                 130

TAC TTG TTA ACT ATC AAA GAA CTC AAA TAT CCT CAA CTC TTT GAT TTA    665
Tyr Leu Leu Thr Ile Lys Glu Leu Lys Tyr Pro Gln Leu Phe Asp Leu
135                 140                 145                 150

ACT AAT CAT ATG TTA ACT TTG TGT GAT AAT ATT CAT GGT TTC AAA TAT    713
Thr Asn His Met Leu Thr Leu Cys Asp Asn Ile His Gly Phe Lys Tyr
                155                 160                 165

TTA ATT GAT GGA TAT GAA GAA ATT AAT GAA TTA TTA TAT AAA TTA AAC    761
Leu Ile Asp Gly Tyr Glu Glu Ile Asn Glu Leu Leu Tyr Lys Leu Asn
                170                 175                 180

TTT TAT TTT GAT TTA TTA AGA GCA AAA TTA AAT GAT GTA TGT GCT AAT    809
Phe Tyr Phe Asp Leu Leu Arg Ala Lys Leu Asn Asp Val Cys Ala Asn
            185                 190                 195
```

Fig. 1B

```
GAT TAT TGT CAA ATA CCT TTC AAT CTT AAA ATT CGT GCA AAT GAA TTA        857
Asp Tyr Cys Gln Ile Pro Phe Asn Leu Lys Ile Arg Ala Asn Glu Leu
    200             205             210

GAC GTA CTT AAA AAA CTT GTG TTC GGA TAT AGA AAA CCA TTA GAC AAT        905
Asp Val Leu Lys Lys Leu Val Phe Gly Tyr Arg Lys Pro Leu Asp Asn
215             220             225             230

ATT AAA GAT AAT GTA GGA AAA ATG GAA GAT TAC ATT AAA AAA AAT AAA        953
Ile Lys Asp Asn Val Gly Lys Met Glu Asp Tyr Ile Lys Lys Asn Lys
            235             240             245

AAA ACC ATA GAA AAT ATA AAT GAA TTA ATT GAA GAA AGT AAG AAA ACA       1001
Lys Thr Ile Glu Asn Ile Asn Glu Leu Ile Glu Glu Ser Lys Lys Thr
        250             255             260

ATT GAT AAA AAT AAG AAT GCA ACT AAA GAA GAA GAA AAA AAA AAA TTA       1049
Ile Asp Lys Asn Lys Asn Ala Thr Lys Glu Glu Glu Lys Lys Lys Leu
        265             270             275

TAC CAA GCT CAA TAT GAT CTT TCT ATT TAC AAT AAA CAA TTA GAA GAA       1097
Tyr Gln Ala Gln Tyr Asp Leu Ser Ile Tyr Asn Lys Gln Leu Glu Glu
    280             285             290

GCA CAT AAT TTA ATA AGC GTT TTA GAA AAA CGT ATT GAC ACT TTA AAA       1145
Ala His Asn Leu Ile Ser Val Leu Glu Lys Arg Ile Asp Thr Leu Lys
295             300             305             310

AAA AAT GAA AAC ATT AAG GAA TTA CTT GAT AAG ATA AAT GAA ATT AAA       1193
Lys Asn Glu Asn Ile Lys Glu Leu Leu Asp Lys Ile Asn Glu Ile Lys
            315             320             325

AAT CCC CCA CCG GCC AAT TCT GGA AAT ACA CCA AAT ACT CTC CTT GAT       1241
Asn Pro Pro Pro Ala Asn Ser Gly Asn Thr Pro Asn Thr Leu Leu Asp
        330             335             340

AAG AAC AAA AAA ATC GAG GAA CAC GAA AAA GAA ATA AAA GAA ATT GCC       1289
Lys Asn Lys Lys Ile Glu Glu His Glu Lys Glu Ile Lys Glu Ile Ala
        345             350             355

AAA ACT ATT AAA TTT AAT ATT GAT AGT TTA TTT ACT GAT CCA CTT GAA       1337
Lys Thr Ile Lys Phe Asn Ile Asp Ser Leu Phe Thr Asp Pro Leu Glu
    360             365             370

TTA GAA TAC TAT TTA AGA GAA AAA AAT AAA AAT ATT GAT ATA AGT GCA       1385
Leu Glu Tyr Tyr Leu Arg Glu Lys Asn Lys Asn Ile Asp Ile Ser Ala
375             380             385             390

AAG GTT GAA ACA AAG GAA TCA ACT GAA CCC AAT GAA TAT CCA AAT GGA       1433
Lys Val Glu Thr Lys Glu Ser Thr Glu Pro Asn Glu Tyr Pro Asn Gly
            395             400             405

GTT ACT TAT CCT TTG TCA TAT AAC GAT ATT AAC AAT GCT TTA AAT GAA       1481
Val Thr Tyr Pro Leu Ser Tyr Asn Asp Ile Asn Asn Ala Leu Asn Glu
        410             415             420
```

Fig. 1C

| | |
|---|---|
| CTT AAT TCT TTT GGT GAT TTA ATT AAT CCA TTT GAT TAT ACA AAA GAA<br>Leu Asn Ser Phe Gly Asp Leu Ile Asn Pro Phe Asp Tyr Thr Lys Glu<br>            425                       430                       435 | 1529 |
| CCA AGT AAA AAC ATA TAT ACT GAT AAT GAA AGA AAA AAA TTC ATA AAT<br>Pro Ser Lys Asn Ile Tyr Thr Asp Asn Glu Arg Lys Lys Phe Ile Asn<br>440                       445                       450 | 1577 |
| GAA ATT AAG GAA AAA ATT AAA ATA GAA AAA AAA AAA ATT GAA TCT GAT<br>Glu Ile Lys Glu Lys Ile Lys Ile Glu Lys Lys Lys Ile Glu Ser Asp<br>455                     460                  465                  470 | 1625 |
| AAA AAA TCT TAC GAA GAC AGA TCT AAG TCT TTA AAT GAT ATA ACA AAA<br>Lys Lys Ser Tyr Glu Asp Arg Ser Lys Ser Leu Asn Asp Ile Thr Lys<br>                     475                       480                  485 | 1673 |
| GAA TAT GAA AAA TTA CTT AAT GAA ATT TAT GAT AGC AAA TTC AAT AAT<br>Glu Tyr Glu Lys Leu Leu Asn Glu Ile Tyr Asp Ser Lys Phe Asn Asn<br>             490                       495                       500 | 1721 |
| AAT ATA GAT TTA ACT AAT TTC GAA AAA ATG ATG GGT AAA AGA TAT TCA<br>Asn Ile Asp Leu Thr Asn Phe Glu Lys Met Met Gly Lys Arg Tyr Ser<br>         505                       510                  515 | 1769 |
| TAT AAA GTT GAG AAA CTT ACA CAC CCT AAT ACT TTT GCA TCC TAT GAA<br>Tyr Lys Val Glu Lys Leu Thr His Pro Asn Thr Phe Ala Ser Tyr Glu<br>     520                     525                     530 | 1817 |
| AAT TCT AAA CAT AAT CTT GAA AAG TTA ACA AAA GCT CTT AAA TAT ATG<br>Asn Ser Lys His Asn Leu Glu Lys Leu Thr Lys Ala Leu Lys Tyr Met<br>535                     540                  545                  550 | 1865 |
| GAA GAT TAT TCT TTA AGG AAT ATA GTA GTT GAA AAA GAA TTA AAA TAT<br>Glu Asp Tyr Ser Leu Arg Asn Ile Val Val Glu Lys Glu Leu Lys Tyr<br>             555                       560                  565 | 1913 |
| TAT AAA AAT TTA ATA AGC AAA ATA GAA AAT GAG ATT GAA ACA TTA GTT<br>Tyr Lys Asn Leu Ile Ser Lys Ile Glu Asn Glu Ile Glu Thr Leu Val<br>         570                       575                  580 | 1961 |
| GAA AAT ATT AAA AAA GAT GAA GAA CAG CTT TTT GAA AAA AAA ATT ACT<br>Glu Asn Ile Lys Lys Asp Glu Glu Gln Leu Phe Glu Lys Lys Ile Thr<br>             585                       590                  595 | 2009 |
| AAA GAC GAA AAT AAA CCA GAT GAA AAA ATT TTA GAA GTA TCT GAC ATT<br>Lys Asp Glu Asn Lys Pro Asp Glu Lys Ile Leu Glu Val Ser Asp Ile<br>     600                     605                     610 | 2057 |
| GTA AAA GTA CAA GTT CAA AAA GTT TTA TTA ATG AAC AAA ATT GAC GAA<br>Val Lys Val Gln Val Gln Lys Val Leu Leu Met Asn Lys Ile Asp Glu<br>615                     620                  625                  630 | 2105 |
| TTA AAA AAG ACT CAA TTG ATT TTA AAA AAT GTA GAA TTA AAA CAT AAT<br>Leu Lys Lys Thr Gln Leu Ile Leu Lys Asn Val Glu Leu Lys His Asn<br>             635                       640                  645 | 2153 |

Fig. 1D

```
ATA CAT GTT CCC AAT TCT TAC AAA CAA GAA AAT AAG CAA GAA CCT TAT        2201
Ile His Val Pro Asn Ser Tyr Lys Gln Glu Asn Lys Gln Glu Pro Tyr
            650                 655                 660

TAT TTA ATT GTG TTG AAA AAA GAA ATT GAT AAA TTA AAA GTG TTC ATG        2249
Tyr Leu Ile Val Leu Lys Lys Glu Ile Asp Lys Leu Lys Val Phe Met
            665                 670                 675

CCT AAG GTA GAA TCA TTG ATA AAT GAA GAA AAA AAA AAC ATA AAA ACA        2297
Pro Lys Val Glu Ser Leu Ile Asn Glu Glu Lys Lys Asn Ile Lys Thr
            680                 685                 690

CAA GGT CAA TCG GAT AAT TCG GAA CCA TCA ACC GAA GGA GAA ATA ACA        2345
Gln Gly Gln Ser Asp Asn Ser Glu Pro Ser Thr Glu Gly Glu Ile Thr
695             700                 705                 710

GGA CAA GCA ACT ACA AAA CCT GGA CAA CAA GCA GGA TCT GCT TTA GAA        2393
Gly Gln Ala Thr Thr Lys Pro Gly Gln Gln Ala Gly Ser Ala Leu Glu
                715                 720                 725

GGA GAT TCA GTA CAA GCA CAA GCA CAA GAA CAA AAA CAA GCA CAA CCA        2441
Gly Asp Ser Val Gln Ala Gln Ala Gln Glu Gln Lys Gln Ala Gln Pro
            730                 735                 740

CCA GTA CCA GTA CCA GTA CCA GAA GCA AAA GCA CAA GTC CCA ACA CCA        2489
Pro Val Pro Val Pro Val Pro Glu Ala Lys Ala Gln Val Pro Thr Pro
            745                 750                 755

CCA GCA CCA GTA AAT AAT AAA ACT GAA AAT GTT TCC AAA TTA GAT TAT        2537
Pro Ala Pro Val Asn Asn Lys Thr Glu Asn Val Ser Lys Leu Asp Tyr
            760                 765                 770

CTT GAA AAA TTA TAT CAA TTT TTA AAT ACT TCA TAT ATA TGT CAC AAA        2585
Leu Glu Lys Leu Tyr Gln Phe Leu Asn Thr Ser Tyr Ile Cys His Lys
775                 780                 785                 790

TAT ATT TTG GTT TCA CAC TCA ACT ATG AAC GAA AAG ATA TTA AAA CAA        2633
Tyr Ile Leu Val Ser His Ser Thr Met Asn Glu Lys Ile Leu Lys Gln
                795                 800                 805

TAT AAA ATT ACA AAG GAG GAA GAA AGC AAA TTA AGT TCA TGT GAT CCA        2681
Tyr Lys Ile Thr Lys Glu Glu Glu Ser Lys Leu Ser Ser Cys Asp Pro
            810                 815                 820

TTA GAC TTA TTG TTT AAT ATA CAA AAT AAC ATA CCT GTA ATG TAT TCT        2729
Leu Asp Leu Leu Phe Asn Ile Gln Asn Asn Ile Pro Val Met Tyr Ser
            825                 830                 835

ATG TTT GAT AGC TTA AAC ATA GTT TAT CAC AAC TAT TTA TGG GTT TAT        2777
Met Phe Asp Ser Leu Asn Ile Val Tyr His Asn Tyr Leu Trp Val Tyr
            840                 845                 850

GAA AAA GAA ATT GGT TAT GTA TTT ATA TTA CTT ATG GAA ATT TAT GAA        2825
Glu Lys Glu Ile Gly Tyr Val Phe Ile Leu Leu Met Glu Ile Tyr Glu
855                 860                 865                 870
```

Fig. 1E

| | |
|---|---|
| AAA GAA ATG GTT TGT AAT TTA TAT AAA CTT AAG GAT AAT GAC AAA ATT<br>Lys Glu Met Val Cys Asn Leu Tyr Lys Leu Lys Asp Asn Asp Lys Ile<br>            875                    880                   885 | 2873 |
| AAA AAT TTA TTA GAG GAA GCG AAA AAA GTA TCC ACA TCT GTA AAA ACT<br>Lys Asn Leu Leu Glu Glu Ala Lys Lys Val Ser Thr Ser Val Lys Thr<br>            890                    895                   900 | 2921 |
| CTT TCA AGT TCA TCA ATG CAA CCA TTA TCA TTA ACA CCT CAG GAT AAA<br>Leu Ser Ser Ser Ser Met Gln Pro Leu Ser Leu Thr Pro Gln Asp Lys<br>            905                    910                   915 | 2969 |
| CCC GAA GTA AGT GCA AAT GAT GAT ACA TCA CAT TCT ACA AAT TTG AAT<br>Pro Glu Val Ser Ala Asn Asp Asp Thr Ser His Ser Thr Asn Leu Asn<br>            920                    925                   930 | 3017 |
| AAT AGT TTA AAA TTA TTT GAA AAC ATA TTG AGT CTT GGA AAA AAC AAA<br>Asn Ser Leu Lys Leu Phe Glu Asn Ile Leu Ser Leu Gly Lys Asn Lys<br>935                   940                    945                   950 | 3065 |
| AAT ATA TAC CAA GAA TTA ATA GGT CAA AAA AGT AGT GAA AAC TTT TAT<br>Asn Ile Tyr Gln Glu Leu Ile Gly Gln Lys Ser Ser Glu Asn Phe Tyr<br>            955                    960                   965 | 3113 |
| GAA AAG ATA TTA AAA GAT AGT GAT ACA TTT TAT AAT GAA TCT TTT ACA<br>Glu Lys Ile Leu Lys Asp Ser Asp Thr Phe Tyr Asn Glu Ser Phe Thr<br>            970                    975                   980 | 3161 |
| AAT TTT GTA AAA TCT AAA GCT GAT GAT ATT AAT TCA TTG AAT GAT GAA<br>Asn Phe Val Lys Ser Lys Ala Asp Asp Ile Asn Ser Leu Asn Asp Glu<br>            985                    990                   995 | 3209 |
| TCA AAA AGG AAG AAA TTA GAA GAA GAT ATT AAT AAA TTA AAA AAA ACT<br>Ser Lys Arg Lys Lys Leu Glu Glu Asp Ile Asn Lys Leu Lys Lys Thr<br>           1000                  1005                  1010 | 3257 |
| TTA CAG TTA TCA TTT GAT TTA TAT AAT AAA TAT AAA TTA AAA TTA GAA<br>Leu Gln Leu Ser Phe Asp Leu Tyr Asn Lys Tyr Lys Leu Lys Leu Glu<br>1015               1020                  1025                  1030 | 3305 |
| AGA TTA TTT GAT AAA AAG AAA ACA GTT GGT AAA TAT AAA ATG CAA ATT<br>Arg Leu Phe Asp Lys Lys Lys Thr Val Gly Lys Tyr Lys Met Gln Ile<br>               1035                  1040                  1045 | 3353 |
| AAA AAA CTT ACT TTA TTA AAA GAA CAA TTA GAA TCA AAA TTG AAT TCA<br>Lys Lys Leu Thr Leu Leu Lys Glu Gln Leu Glu Ser Lys Leu Asn Ser<br>           1050                  1055                  1060 | 3401 |
| CTT AAT AAC CCA AAG CAT GTA TTA CAA AAC TTT TCT GTT TTC TTT AAC<br>Leu Asn Asn Pro Lys His Val Leu Gln Asn Phe Ser Val Phe Phe Asn<br>           1065                  1070                  1075 | 3449 |
| AAA AAA AAA GAA GCT GAA ATA GCA GAA ACT GAA AAC ACA TTA GAA AAC<br>Lys Lys Lys Glu Ala Glu Ile Ala Glu Thr Glu Asn Thr Leu Glu Asn<br>           1080                  1085                  1090 | 3497 |

Fig. 1F

```
ACA AAA ATA TTA TTG AAA CAT TAT AAA GGA CTT GTT AAA TAT TAT AAT         3545
Thr Lys Ile Leu Leu Lys His Tyr Lys Gly Leu Val Lys Tyr Tyr Asn
1095                1100                1105                1110

GGT GAA TCA TCT CCA TTA AAA ACT TTA AGT GAA GAA TCA ATT CAA ACA         3593
Gly Glu Ser Ser Pro Leu Lys Thr Leu Ser Glu Glu Ser Ile Gln Thr
                    1115                1120                1125

GAA GAT AAT TAT GCC AGT TTA GAA AAC TTT AAA GTA TTA AGT AAA TTA         3641
Glu Asp Asn Tyr Ala Ser Leu Glu Asn Phe Lys Val Leu Ser Lys Leu
            1130                1135                1140

GAA GGA AAA TTA AAG GAT AAT CTA AAT TTA GAA AAG AAA AAA TTA TCA         3689
Glu Gly Lys Leu Lys Asp Asn Leu Asn Leu Glu Lys Lys Lys Leu Ser
        1145                1150                1155

TAC TTA TCA AGA GGT TTA CAT CAT TTA ATT GCT GAA TTA AAA GAA GTA         3737
Tyr Leu Ser Arg Gly Leu His His Leu Ile Ala Glu Leu Lys Glu Val
    1160                1165                1170

ATA AAA AAT AAA AAT TAT ACA GGT AAT TCT CCA AGC GTA AAT AAT ACG         3785
Ile Lys Asn Lys Asn Tyr Thr Gly Asn Ser Pro Ser Val Asn Asn Thr
1175                1180                1185                1190

GAT GTT AAC AAT GCA TTA GAA TCT TAC AAA AAA TTT CTC CCA GAA GGA         3833
Asp Val Asn Asn Ala Leu Glu Ser Tyr Lys Lys Phe Leu Pro Glu Gly
                    1195                1200                1205

ACA GAT GTT GCA ACA GTT GTA AGT GAA AGT GGA TCC GAC ACA TTA GAA         3881
Thr Asp Val Ala Thr Val Val Ser Glu Ser Gly Ser Asp Thr Leu Glu
            1210                1215                1220

CAA AGT CAA CCA AAG AAA CCA GCA TCA ACT CAT GTA GGA GCA GAG TCT         3929
Gln Ser Gln Pro Lys Lys Pro Ala Ser Thr His Val Gly Ala Glu Ser
        1225                1230                1235

AAC ACA ATA ACA ACA TCA CAA AAT GTC GAT GAT GAA GTA GAT GAC GTA         3977
Asn Thr Ile Thr Thr Ser Gln Asn Val Asp Asp Glu Val Asp Asp Val
    1240                1245                1250

ATC ATA GTA CTC ATA TTT GGA GAA TCC GAA GAA GAT TAT GAT GAT TTA         4025
Ile Ile Val Leu Ile Phe Gly Glu Ser Glu Glu Asp Tyr Asp Asp Leu
1255                1260                1265                1270

GGA CAA GTA GTA ACA GGA GAA GCA GTA ACT ACT TCC GTA ATT GAT AAC         4073
Gly Gln Val Val Thr Gly Glu Ala Val Thr Thr Ser Val Ile Asp Asn
                    1275                1280                1285

ATA CTT TCT AAA ATT GAA AAT GAA TAT GAG GTT TTA TAT TTA AAA CCT         4121
Ile Leu Ser Lys Ile Glu Asn Glu Tyr Glu Val Leu Tyr Leu Lys Pro
            1290                1295                1300

TTA GCA GGT GTT TAT AGA AGT TTA AAA AAA CAA TTA GAA AAT AAC GTT         4169
Leu Ala Gly Val Tyr Arg Ser Leu Lys Lys Gln Leu Glu Asn Asn Val
        1305                1310                1315
```

Fig. 1G

```
ATG ACA TTT AAT GTT AAT GTT AAG GAT ATT TTA AAT TCA CGA TTT AAT        4217
Met Thr Phe Asn Val Asn Val Lys Asp Ile Leu Asn Ser Arg Phe Asn
    1320            1325            1330

AAA CGT GAA AAT TTC AAA AAT GTT TTA GAA TCA GAT TTA ATT CCA TAT        4265
Lys Arg Glu Asn Phe Lys Asn Val Leu Glu Ser Asp Leu Ile Pro Tyr
1335            1340            1345            1350

AAA GAT TTA ACA TCA AGT AAT TAT GTT GTC AAA GAT CCA TAT AAA TTT        4313
Lys Asp Leu Thr Ser Ser Asn Tyr Val Val Lys Asp Pro Tyr Lys Phe
                1355            1360            1365

CTT AAT AAA GAA AAA AGA GAT AAA TTC TTA AGC AGT TAT AAT TAT ATT        4361
Leu Asn Lys Glu Lys Arg Asp Lys Phe Leu Ser Ser Tyr Asn Tyr Ile
            1370            1375            1380

AAG GAT TCA ATA GAT ACG GAT ATA AAT TTT GCA AAT GAT GTT CTT GGA        4409
Lys Asp Ser Ile Asp Thr Asp Ile Asn Phe Ala Asn Asp Val Leu Gly
            1385            1390            1395

TAT TAT AAA ATA TTA TCC GAA AAA TAT AAA TCA GAT TTA GAT TCA ATT        4457
Tyr Tyr Lys Ile Leu Ser Glu Lys Tyr Lys Ser Asp Leu Asp Ser Ile
    1400            1405            1410

AAA AAA TAT ATC AAC GAC AAA CAA GGT GAA AAT GAG AAA TAC CTT CCC        4505
Lys Lys Tyr Ile Asn Asp Lys Gln Gly Glu Asn Glu Lys Tyr Leu Pro
1415            1420            1425            1430

TTT TTA AAC AAT ATT GAG ACC TTA TAT AAA ACA GTT AAT GAT AAA ATT        4553
Phe Leu Asn Asn Ile Glu Thr Leu Tyr Lys Thr Val Asn Asp Lys Ile
                1435            1440            1445

GAT TTA TTT GTA ATT CAT TTA GAA GCA AAA GTT CTA AAT TAT ACA TAT        4601
Asp Leu Phe Val Ile His Leu Glu Ala Lys Val Leu Asn Tyr Thr Tyr
            1450            1455            1460

GAG AAA TCA AAC GTA GAA GTT AAA ATA AAA GAA CTT AAT TAC TTA AAA        4649
Glu Lys Ser Asn Val Glu Val Lys Ile Lys Glu Leu Asn Tyr Leu Lys
            1465            1470            1475

ACA ATT CAA GAC AAA TTG GCA GAT TTT AAA AAA AAT AAC AAT TTC GTT        4697
Thr Ile Gln Asp Lys Leu Ala Asp Phe Lys Lys Asn Asn Asn Phe Val
    1480            1485            1490

GGA ATT GCT GAT TTA TCA ACA GAT TAT AAC CAT AAT AAC TTA TTG ACA        4745
Gly Ile Ala Asp Leu Ser Thr Asp Tyr Asn His Asn Asn Leu Leu Thr
1495            1500            1505            1510

AAG TTC CTT AGT ACA GGT ATG GTT TTT GAA AAC TTG CTA AAA TCC GTT        4793
Lys Phe Leu Ser Thr Gly Met Val Phe Glu Asn Leu Leu Lys Ser Val
                1515            1520            1525

TTA TCT AAT TTA CTT GAT TGG AAA CTT GCA AGG TAT GTT AAA CAT TTC        4841
Leu Ser Asn Leu Leu Asp Trp Lys Leu Ala Arg Tyr Val Lys His Phe
            1530            1535            1540
```

Fig. 1H

```
ACA ACA CCA ATG CGT AAA AAA ACA ATG ATC CAA CAG AGT TCT GGA TGT      4889
Thr Thr Pro Met Arg Lys Lys Thr Met Ile Gln Gln Ser Ser Gly Cys
        1545            1550            1555

TTC AGA CAT TTA GAT GAA AGA GAA GAA TGT AAA TGT TTA TTA AAT TAC      4937
Phe Arg His Leu Asp Glu Arg Glu Glu Cys Lys Cys Leu Leu Asn Tyr
        1560            1565            1570

AAA CAA GAA GGT AGT AAA TGT GTT GAA AAT TCA AAT CCT ACT TGT AAC      4985
Lys Gln Glu Gly Ser Lys Cys Val Glu Asn Ser Asn Pro Thr Cys Asn
1575            1580            1585            1590

GAA AAT AAT GGT GGA TGT GAT GCA GAT GCC AAA TGT ACC GAA GAA GAT      5033
Glu Asn Asn Gly Gly Cys Asp Ala Asp Ala Lys Cys Thr Glu Glu Asp
                1595            1600            1605

TCA GGT AGC AAC GGA AAG AAA ATC ACA TGT GAA TGT ACT AAA CCT GAT      5081
Ser Gly Ser Asn Gly Lys Lys Ile Thr Cys Glu Cys Thr Lys Pro Asp
            1610            1615            1620

TGT TAT CCA CTT TCG ATG GTA ATT TTC TGC AGT TCC TCT AAC TTC TTA      5129
Cys Tyr Pro Leu Ser Met Val Ile Phe Cys Ser Ser Ser Asn Phe Leu
        1625            1630            1635

GGA ATA TCA TTC TTA TTA ATA CTC ATG TTA ATA TTA TAC AGT TTC ATT T    5178
Gly Ile Ser Phe Leu Leu Ile Leu Met Leu Ile Leu Tyr Ser Phe Ile
        1640            1645            1650

AAAAAATGTA GGAGTTAAAA TATGTTACCT TAATTTTTTT TTTTTTTTTT TTTTTTAAAT    5238

ATATATATAT ATTAATATAT ATATATAAAA TATTACATAA TATATATATA TATATTTAGT    5298

TATTACAGGA ATAGTGATAT TTTAGTCATG TTCAAAATAT ATTAAAAAAT TATAAATATT    5358

ATAATAAAAA AAAAAAAAAA AAAAAATTAT ATACTTATAA ATTTATACAT TTATACATAT    5418

ATATATATAT ATTTTTTTTT CTTCTTTCTT TTCAAGTTCT ATTTTATATT TTATATATAG    5478

ATTTAATAAA AAACTTTTTA AAATAAAAAA AAGTACGTAA ATTTTAATAT ATATATATAT    5538

ATATATAATA TATATATAAT ATATATTTAT TTATTTATAT GTATAATATA TTTACATATA    5598

TTATTATAAT ATATATATTT TTTTTTACGC ATACATAAAA AGCATTTTTT TTTTTTATAA    5658

ACATTCCAAC AATTATAAAA TAACTTTAAT AATAACATTA AATTTTTATT TTTTTTTTTA    5718

AAAAAAAAAA AAAAAAAAAA AAAAAACTAA AGAGATTATT CA                      5760
```

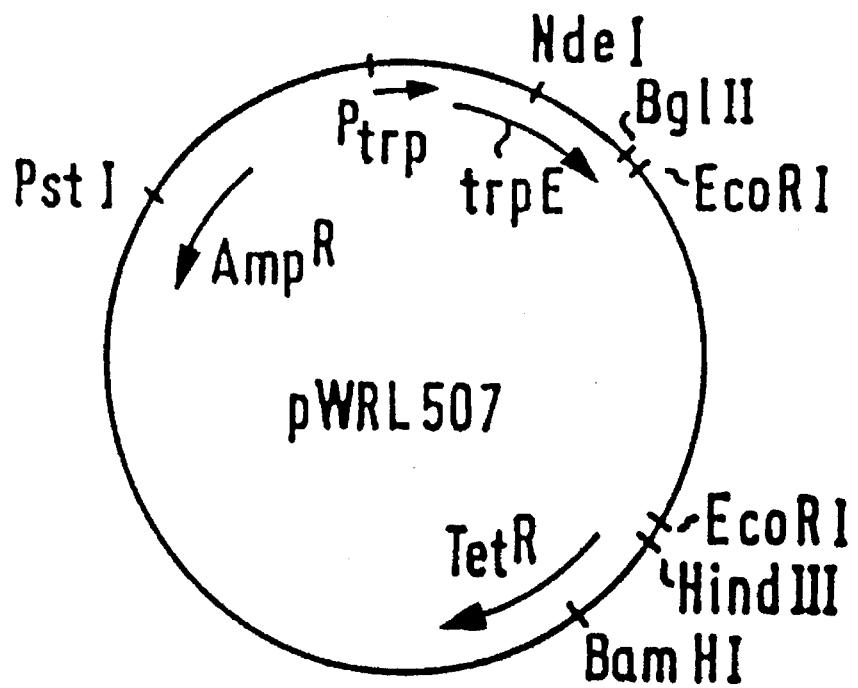
Fig. 4
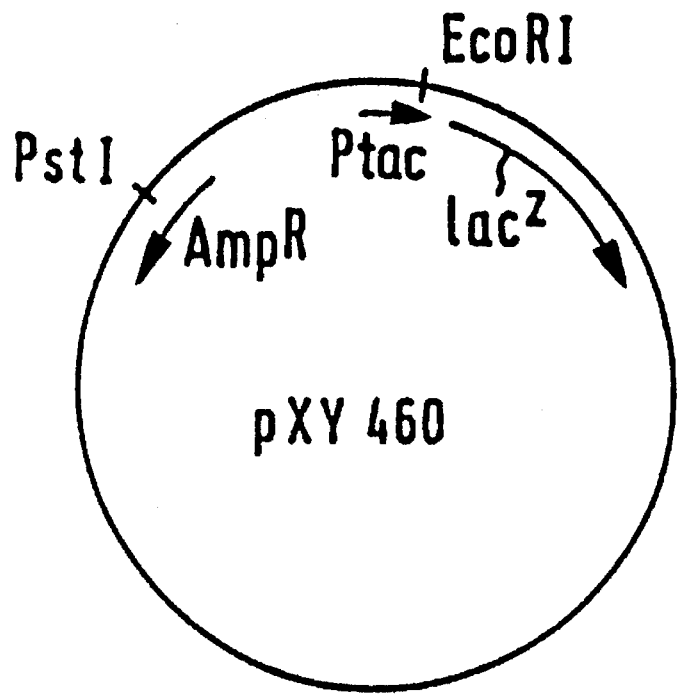

CLONING OF A MALARIAL GENE

This is a continuation of application Ser. No. 07/985,448, filed Dec. 3, 1992 now abandoned; which is a continuation of Ser. No. 07/678,900, filed Mar. 28, 1991, now abandoned; which is a continuation of Ser. No. 07/108,273, filed Oct. 13, 1987, now abandoned; which is a division of Ser. No. 06/703,663, filed Feb. 21, 1985, now abandoned.

The present invention relates to a cloned sequence of DNA, and fragments thereof, of *Plasmodium falciparum* which may be used to provide antigenic peptides for use in malaria vaccines.

Malaria is an increasing health problem throughout the third world. Several hundred million people suffer from the disease and the most acute form, caused by the protozoan parasite *Plasmodium falciparum*, kills over a million children each year in Africa alone. An effective immunity against the sexual multiplication of the parasite in the blood-stream would prevent the clinical disease. Prevention of the re-invasion of red blood cells by an effective immune response against the invasive form, the merozoite, should interrupt this cycle.

In a rodent malarial model it has been shown that a protein antigen synthesized within the mature intraerythrocytic form, the schizont, and expressed on the surface of the merozoite, can be purified and that vaccination with this antigen can generate protective immunity against *Plasmodium yoelii* (Holder, A. A. and Freeman, R. R. Nature 294, 361–364 (1981)). This antigen has an apparent molecular weight (MW) of 230,000 and is proteolytically processed in vivo such that discrete fragments of the antigen are present on the merozoite surface (Holder and Freeman, 1981 supra; Holder, A. A. and Freeman, R. R. Parasitology 88, 211–219 (1984a)).

By "molecular weight" is meant the apparent relative molecular weight as determined by polyacrylamide gel electrophoresis in the presence of sodium dodecyl sulphate and standard molecular weight markers. The molecular weight of the antigenic proteins of the invention may thus be conveniently determined by the techniques described by U. K. Laemmli, *Nature*, (1970) 227, 680–685. Convenient standard molecular weight markers include, for example, spectrin heterodimer ($2.2 \times 10^5$ M.W.), β-galactosidase ($1.16 \times 10^5$ MW), phosphorylase b ($9.3 \times 10^4$ MW), bovine serum albumin ($6.8'10^4$ MW), aldolase ($3.9 \times 10^4$ MW), triose phosphate isomerase ($2.7'10^4$ MW) and lysozyme ($1.5 \times 10^4$ MW).

When the protein was used to vaccinate mice the protection was adjuvant dependent and it appeared to be provided by a cell mediated effector pathway (Freeman, R. R. and Holder, A. A. Clin. Exp. Immunol. 54, 609–616 (1983a)), although a monoclonal antibody against the protein has been shown to confer passive protection upon mice (Majariam W. R. et al., J. Immunol. 132, 3131–3137 (1984)).

Analogous protein antigens have also been described in other Plasmodium species. A polyvalent antiserum raised against the purified 230,000 MW antigen of *P. yoelii* cross-reacted by immunofluorescence with the blood stage forms of all other species of Plasmodium tested (Holder and Freeman, 1984a, supra). In *Plasmodium chabaudi* the antigen was identified by Western blotting as a 250,000 MW species which may also be processed (Holder, A. A. et al., Mol. Biochem. Parasitol. 9, 191–196 (1983)). Monoclonal antibodies specific for the 250,000 MW *P. chabaudi* protein were shown to confer passive protection against *P. chabaudi* challenge in mice (Boyle, D. B. et al., Infect Immun. 38, 94–102 (1982)). A monoclonal antibody against a 230,000 MW protein of *Plasmodium knowlesi* agglutinated merozoites and thereby inhibited parasite invasion of red cells in vitro (Epstein N. et al., J. Immunol. 127, 212–217 (1981)), and this protein of *P. knowlesi* is processed in vivo to a series of fragments expressed on the merozoite surface (David P. H. et al., Mol. Biochem. Parasitol. 11, 267–282 (1984)).

In *P. falciparum*, polyvalent antiserum against the *P. yoelii* 230,000 MW protein antigen cross-reacted with a 195,000 MW antigen (hereinafter referred to as the P.195 protein) (Holder et al., (1983) supra). The biosynthesis of this antigen, which appears to be a glycoprotein (Howard, R. J. et al., Mol. Biochem. Parasitol. 11, 349–362 (1984)) takes place within the schizont form of the parasite and at the end of the intra-erythrocytic stage the antigen is proteolytically processed into discrete fragments (Holder, A. A. and Freeman, R. R. J. Exp. Med. 156, 1528–1538, (1982); Hall, R. et al., Mol. Biochem, Parasitol. 11, 61–80 (1984a)). On the surface of the merozoites (released into the serum at the end of the intra-erythrocytic stage), the protein is fully processed, with three discrete fragments of P.195 having molecular weights of about 83,000, 42,000 and 19,000 being present. These three fragments are the major surface antigens of merozoites and are strongly recognised by human Immune serum (Freeman, R. R. and Holder, A. A. J. Exp. Med. 158, 1647–1653 (1983b), Holder, A. A. and Freeman R. R. J. Exp. Med. 160, 624–629 (1984b)).

The term 'P.195' is used herein to denote a protein of between 1.8 and $2.3 \times 10^5$ MW which is localised in the erythrocytic schizont form of a *Plasmodium falciparum* parasite and which is processed in vivo into discrete fragments of approximately $8.3 \times 10^4$, $4.2 \times 10^4$ and $1.9 \times 10^4$ MW, associated with the surface membranes of the merozoite form of the parasite.

Within *P. falciparum* P.195 may exhibit some structural polymorphism as detected by the degree of binding of specific monoclonal antibodies or by small differences in its apparent molecular weight (McBride, J. S. et al., Science 217, 254–257 (1982); McBride, J. S. et al., Trans. Roy. Soc. Trop. Med. Hyg. 78, 32–34 (1984); Hall, R et al., (1984a) supra). However it will be appreciated by those skilled in the art that these antigens are homologous and that differences demonstrated in particular antigenic determinants may not be important in the broader sense of an immune response in an animal. It has been shown that Saimiri monkeys immunised with P.195 were protected against challenge infection (Perrin, L. H. et al., J. Exp. Med. 160, 441–451 (1984); Hall, R. et al., Nature 311, 379–382 (1984b)).

The term 'epitope' as used herein denotes an immunogenic determinant of an immunogenic molecule, the immunogenic determinant comprising a molecular configuration capable of eliciting a protective immune response in a susceptible animal, when presented in a suitable form.

It will also be appreciated that P.195 is subject to allelic variation, wherein different strains of *P. falciparum* express proteins different from, but substantially similar to any one P.195 protein from any one strain.

A comparison of the P.195 gene from the *P falciparum* strain described herein with the corresponding gene from a strain isolated by Thaithong et al. (Thaithong, S., Beale, G. H., Fenton, B., McBride, J., Rosario, V. Walker, A. and Walliker, D., Trans. Roy. Soc. Trop. Med Hyg. (1984) 78, 242–245) by Southern blotting showed structural polymorphism detectable by nucleic acid hybridisation (R. T. Schwartz).

For the reasons outlined above, it is believed that the *P. falciparum* P.195, or an antigenic fragment thereof, is of value for use in a blood-stage malaria vaccine.

In order to obtain this protein or an antigenic fragment thereof, such as those produced in vivo and which are present on the merozoite surface, in large quantities and in a relatively pure form, it would be desirable to identify the sequence of the DNA in the gene coding for the expression of this protein in *P. falciparum*. After identification of the sequence, it would be desirable to reproduce the immunologically effective parts of the protein molecule, either by cloning this sequence in a suitable vector and expression in a suitable host, or by chemical synthesis of the amino acid sequence corresponding to the identified sequence.

We have now discovered that it is possible to clone the DNA sequence that substantially encodes the above described antigen (P.195) from *P. falciparum* and that the functional antigen or fragments thereof can be obtained by incorporating said cloned DNA into a suitable vector which, in an appropriate host, is capable of expressing the antigen or peptides comprising at least one epitope thereof.

According to one feature of the present invention we therefore provide a cloned DNA sequence substantially encoding the P.195 protein of *P. falciparum*, or peptides comprising at least one epitope thereof.

The term 'cloned' is used herein to indicate any DNA sequence that has been substantially synthesised outside of its natural host.

The term 'peptide' as used herein pertains to any molecular structure composed essentially of amino acids comprising more than 2 amino acids. It will be appreciated that P.195 is a peptide by this definition.

It will be appreciated that the DNA sequences of this invention may correspond to naturally-occurring sequences, or they may be related to such sequences by mutation, including single or multiple base substitutions, deletions, insertions and inversions, always provided that the DNA molecule comprising such a sequence is capable of being expressed as a peptide carrying at least one epitope of the P.195 protein of *P. falciparum*.

The invention will be described in more detail hereinafter with reference to the accompanying drawings in which:

FIG. 1 shows the base sequence of a stretch of *P. falciparum* DNA containing the gene encoding P.195 and the amino acid sequence for which it codes.

FIG. 4 illustrates the construction of plasmids used in the course of exemplifying the invention.

FIGS. 1A to 1H show (in sequence) the nucleotide sequence of the P.195 gene, the amino acid sequence for which it codes and stretches of sequence at either end of the coding sequence. The lower line of each double line of letters represents nucleotides according to convention, while the upper line shows the amino acid sequence for which the open reading frame codes, the letters representing amino acids according to convention. The sequence was determined by methods as accurately as possible within the margins of experimental error, there may be some variation in the P.195 genetic sequence.

Figure 2:
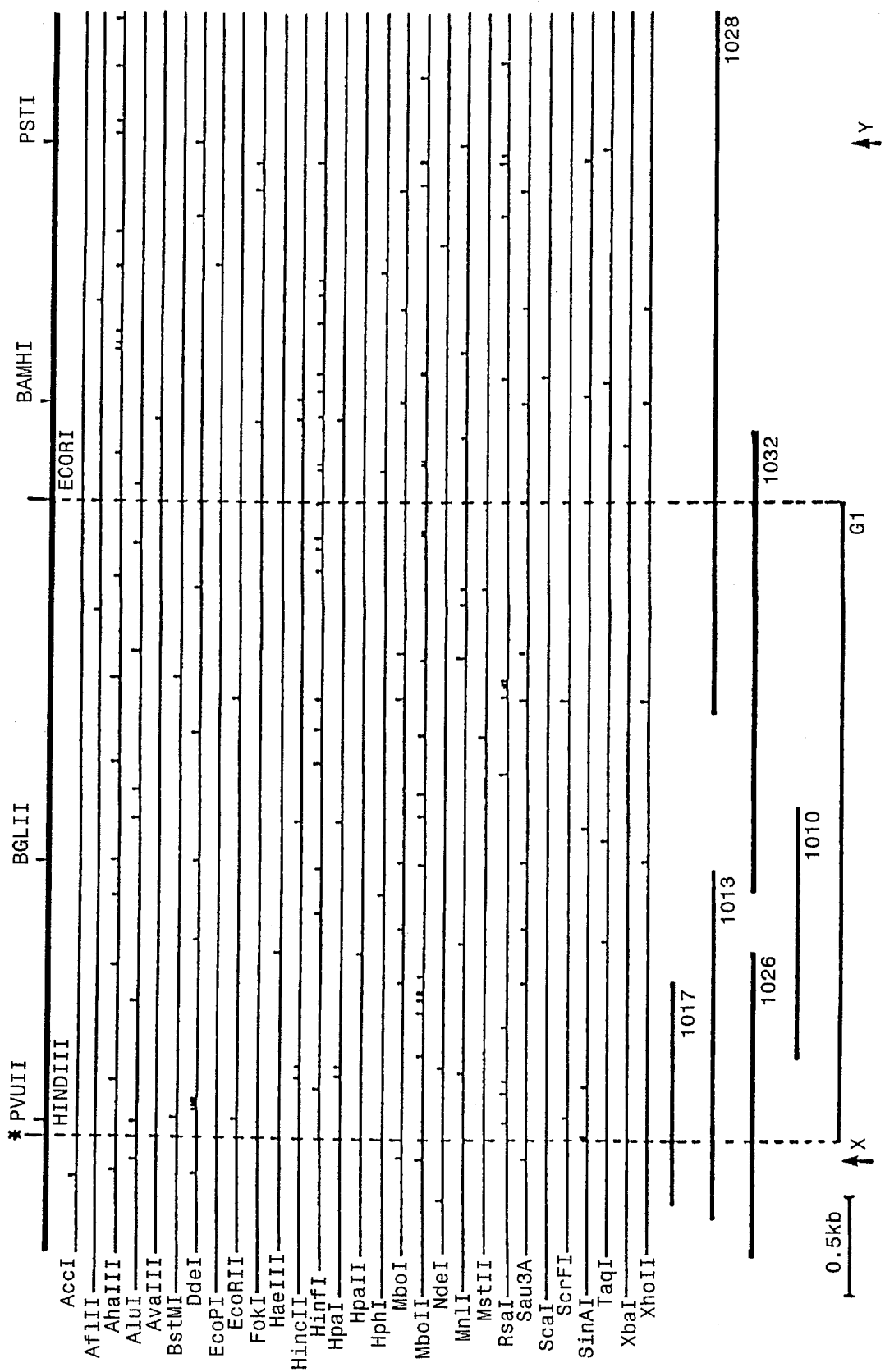
FIG. 2 illustrates a cDNA restriction map of the P.195 gene.

FIG. 2 shows the gene, including sequence in the cDNA clones extending beyond either end of the coding sequence, at the top of the figure (thick line) with important restriction enzyme sites marked. All restriction enzyme codes in this figure are according to convention. Other restriction enzyme sites are indicated on parallel lines below, to simplify the diagram. The blocked-in lines at the bottom of the figure indicate the positions relative to the P.195 gene from which various plasmid inserts derive, all being cDNA inserts except G1, which represents a genomic insert. X and Y indicate the putative 5' and 3' ends of the P.195 coding sequence, respectively.

Figure 3:
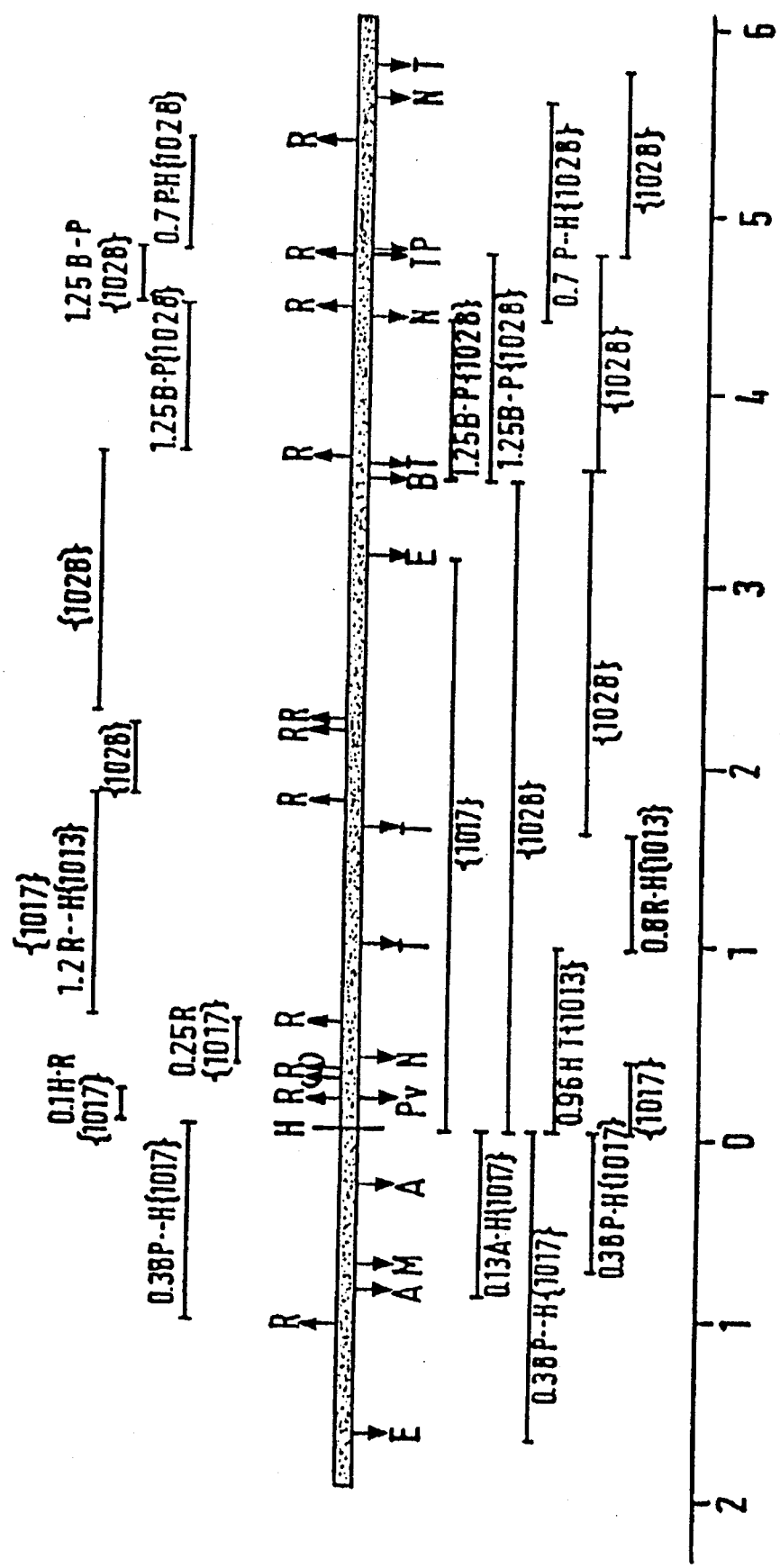
FIG. 3 illustrates a restriction map of the P.195 genomic sequence.

FIG. 3 illustrates a restriction map of the stretch of genomic DNA including the P.195 gene. The scale is in Kbp and takes as its reference point a Hind III restriction site of the P.195 gene indicated by the bold capital H in the figure. The other restriction enzyme sites are coded as follows; E(EcoR1), R(Rsa1), A(Alu1), M(Mbo1), Pv(PvuII), N(Nde1), T(Taq1), B(BamH1) and P(Pst1). The stretches of sequence shown below the restriction map are those that were found to hybridise to the specific clone indicated. The number in brackets is the cDNA clone to which the segment hybridised, the number always corresponding to the relevant pPFc clone. Where there is also a number outside the brackets followed by two of the above-indicated letters, this indicates that the probe used was less than the whole clone, the number indicating the length of the fragment in Kbp and the letters indicate the restriction enzymes used to generate the said fragment.

FIG. 4 illustrates the construction of 2 plasmids used to express fragments of P.195 DNA. pWRL507 has a number of characteristic restriction sites as indicated in the figure, and characteristic gene functions wherein Ptrp, trpE are a promoter and anthranilate synthetase I respectively, $AMP^R$ confers ampicillin resistance and $Tet^R$ confers tetracycline resistance. pXY460 also possesses characteristic restriction sites as indicated, a promoter, (Ptac) a gene coding for βgalactosidase ($lac^Z$) and a gene conferring ampicillin resistance, $Amp^R$.

The above-mentioned DNA sequence may be characterised as having substantially all or part of the sequence shown in FIG. 1, subject to the conditions noted above and further subject to considerations of experimental errors consequent upon determining such a sequence.

The above-mentioned DNA sequence may also be characterised as having substantially the restriction maps as shown in FIGS. 2 and 3, determined as described herein.

The genetic sequence was determined by the chemical cleavage method (Maxam, A., and Gilbert, W Meth. Enzymol 65, 499 (1980)) or by the dideoxy method (Sanger, et al., (1977) Proc. Natl. Acad. Sci., 74, 5463–5467) after sub-cloning fragments of the target DNA into the bacteriophage cloning vectors M13mp8 and M13mp9 (Messing, J and Vieira, J. (1982) Gene 19, 269–276).

Analysis of the sequence shown in FIG. 1 reveals a likely start codon (AUG) at position 216 followed by an open reading frame of a further 1654 codons. The calculated molecular weight of the peptide gene product is 189, 953. The start codon is followed by a putative signal sequence of 18 codons coding for an amino acid sequence which would be cleaved off the protein before it matures. Nucleotides 447–527 code for alternate repeats of the tripeptide sequences serine-glycine-glycine and serine-valine-alanine occuring within the 83,000 MW fragment of P.195 (Example 6). The distribution of some of the amino acids within the translated sequence is asymmetric. For example, of the 19 cysteine residues, two are in the putative signal peptide and eleven are in the C-terminal 97 amino acids (the 42,000 MW Fragment). Eleven tripeptide sequences of the structure Asn-X-Ser or Thr (where X can be any of the common amino acids except proline) have been identified which are potential N-glycosylation sites.

Using the sequence data shown in FIG. 1 it will be appreciated that a peptide corresponding to any part of the sequence may be synthesised using for example, the methods described by Merrifield, R. B., and Marglin, A. (Ann. Rev. Biochem., 39, 841 et seq. (1970)).

Thus, in a further embodiment of the invention, we provide a synthetic peptide comprising at least one epitope of P.195.

The term 'synthetic' as used herein relates to peptides produced by a chemical method as described above, for example.

The identification and cloning of a fragment of the DNA sequence coding for P.195 may be carried out, for example, as follows. Whole messenger RNA (mRNA) was first extracted from synchronous cultures of *P. falciparum* by treating the cells with detergent, precipitating the mRNA by ethanol treatment and centrifugation and purifying by chromatography on oligo-dT cellulose. The substantially pure product was then used to synthesise copy DNA (cDNA) using reverse-transcriptase and DNA polymerase. After purification, the cDNA was inserted into a plasmid which was then introduced into a host by transformation. In order to ascertain which clones in the resulting 'library' contained relevant DNA inserts, a probe was isolated by centrifuging *P. falciparum* mRNA through a sucrose gradient and characterising the fractions by in vitro translation. A fraction found to encode P.195 was rendered radioactive, after limited alkaline hydrolysis, with polynucleotide kinase and $^{32}$P-ATP. Using this probe in a colony hybridisation experiment, several clones were found to hybridise to it, some of them strongly. These were then sorted into families by cross-hybridisation and one of each family was made radioactive by nick-translation with DNA polymerase and $\alpha$-$^{32}$P-dATP. Assuming these probes represent parts of the DNA sequence for P.195, they should hybridise to a mRNA of not less than 5,300 bases long in a total extract of *P. falciparum* mRNA, as this is the minimum estimated length of mRNA necessary to code for a protein of 195,000 MW.

Probes that recognised such mRNA (Northern blot procedure) were then characterised further by incorporation into a vector which, in a suitable host, was capable of expressing the cDNA sequence as a fusion peptide. To ensure expression of this cDNA, the fragments were treated with exonuclease prior to incorporation into the vector in order to give randomised reading frames. Peptides expressed were probed with polyvalent rabbit serum raised against P.195. The DNA fragment referred to above was detected using such a procedure.

With regard to the cloning of full length cDNA for P.195 there are now available several methods for cDNA synthesis to represent the entire mRNA (eg Heidecker, G. and Messing, J. (1983) Nucleic Acid Res. 11, 4891–4906). Cloning may also be carried out by the use of total genomic DNA digest 'libraries' which are prepared readily, and the relevant sequence, or fragments thereof, detected in such a library by the use of the above-described fragment as a 'probe' (for example, Odink, K. G. et al., Mol. Biochem. Parasitol. (1984) 10, 55–66). A proportion of sequences found by this technique may be full length cDNA sequences as required, though many will be fragments of such a sequence. In order to determine which clones in the library represent a part of the DNA sequence desired, a method known as 'chromosome walking' (Hadfield, C., Focus 5, 1–5 (1983) Bethesda Res. Labs.) may be employed, which method entails the use of known fragments (probes) to detect other fragments by cross-hybridisation. These freshly located sequences may then, themselves, be used as probes and, in this way, the whole sequence of DNA substantially encoding P.195 may be identified and cloned. Using such procedures, a restriction map characteristic of the DNA sequence may also be prepared.

The construction of a physical map of the gene for P.195 in genomic DNA by restriction endonuclease cleavage, gel electrophoresis, transfer to nitrocellulose or polyamide membranes and hybridisation to specific probes derived from the cloned DNA is extremely useful to conform and facilitate the orientation and position of cDNA and genomic clones. In addition a comparison of the restriction sites within the cDNA clones with those in the genome can be used to detect features of the gene which may not be present in the mRNA from which the cDNA is synthesized. An example would be the presence of discontinuities within the coding sequence, introns, which may be spliced out of the transcribed RNA by specific splicing events. One such possible intron of about 700 b.p. has been located by the above techniques between nucleotides 221 and 313 of the coding sequence FIG. 1), that is, between the MboI(M) and Hind III sites at these positions (FIG. 3).

As indicated above, P.195 is processed in vivo into discrete fragments including the fragments referred to above. These fragments may prove to be of considerable value in providing immunity against malaria, and the DNA sequences for such fragments represent an important embodiment of the present invention, particularly since such sequences are generally likely to be better capable of expression in suitable vectors than the DNA sequence for the entire protein.

Thus, in a further aspect of the present invention we provide a cloned DNA sequence substantially encoding any one of the P.195 fragments occurring in vivo.

Those fragments of the naturally occurring P.195 most likely to elicit an immune response in a susceptible host are those that are present on the merozoite surface.

In a yet further aspect of the present invention there is provided a cloned DNA sequence substantially encoding any one of the P.195 fragments occurring on the surface membrane of a *P. falciparum* merozoite in vivo.

To locate the position of the processing fragments (Holder and Freeman, 1984b, supra) in the linear gene sequence, one direct approach is to purify the fragments and determine a partial amino acid sequence which can then be compared with the translated gene sequence. This has proved to be feasible for the 83,000 MW fragment which appears to be specifically shed from the merozoite, possibly during the process of red cell invasion, and accumulates in the supernatants of in vitro cultures. Sequencing of the 20 amino-terminal residues of the 83,000 MW fragment of P.195 has also shown that the corresponding coding sequence is located from nucleotides 273 to 332 in FIG. 1, thus positioning this fragment within the gene.

The position of the 42,000 MW fragment was determined by the use of monoclonal antibodies in conventional manner and is described in Example 7. It has been established that the coding sequences for the 42,000 MW and 83,000 MW fragments are at opposite ends of the gene.

Experiments to demonstrate allelic variation in the P.195 gene have shown that the greatest conservation occurs in the region 5' to the Hind III site (in the 83,000 MW fragment) and in the 3' non-coding region (FIG. 2). The most highly conserved sequence is at the 3' end of the gene corresponding to about 130 amino acid residues at the carboxy terminal of the 42,000 MW fragment, suggesting that this fragment may comprise at least one useful epitope.

Thus in a further embodiment of the invention we provide a DNA sequence corresponding to the 42,000 MW fragment of P.195.

The DNA sequence according to the invention may also be used to produce viruses containing the DNA sequence. For example, a strain of vaccinia virus (Tk⁻) unable to confer upon infected cells the ability to grow on media not containing hypoxanthine is used to infect a tissue culture. The tissue culture may then be transformed with the P.195 gene, or fragment(s) thereof, linked to a Tk⁺ genetic determinant. Some of the subsequent viral progeny will have such transforming sequences in the form of inserts in their genomes. These can then be selected by their ability to confer upon tissue culture cells the ability to grow on media devoid of hypoxanthine. Such colonies as do grow are then further selected for production of P.195, or peptides comprising at least one epitope thereof, for example by use of a relevant monoclonal antibody such as F111.2. Such vaccinia strains can then be used to infect animals susceptible to malaria, as the new vaccinia strain will cause production of an immunogenic material peptide(s). Thus, in a yet further aspect of the invention we provide a non-pathogenic virus provided with the DNA sequences according to the invention which may be used to provide immunity to malaria in a susceptible vertebrate host.

It will be appreciated that such vaccines are also readily capable of providing immunity to other infections, such as smallpox, diphtheria, hepatitis B, rabies, herpes simplex virus, whooping cough and the like. Thus, the invention also provides a non-pathogenic virus as defined above, further capable of providing immunity to other infection(s) which may be administered jointly, or individually, together with any other vaccine.

Based on the above-described characterisation of the DNA sequence for P.195, the cloning of any desired fragment of the sequence is possible by reference to the restriction map so gained.

The insertion of a piece of foreign DNA into an *E. coli* gene in the correct reading frame allows the expression of a fusion protein, in which part of the amino acid sequence is derived from the *E. coli* gene and part of it is derived from the inserted DNA. Suitable expression vectors with appropriate control sequences and convenient restriction sites have been constructed, which allow high levels of expression of fusion proteins.

Thus, examination of the restriction map of the expression system of choice and the sequences to be expressed, together with a knowledge of the translational frame, enables specific DNA fragments to be ligated into the expression vector and expressed, without further manipulation. For example, pWRL507 is a plasmid constructed from pAT153 and the trpE gene (Nichols, B. P. et al., J. Mol. biol. 146, 45–54 (1981)) with a synthetic EcoRI-Bgl II linker inserted at the Bgl II site at nucleotide 1223 in the trpE gene (FIG. 4). This vector can be cut with Nde I and EcoRI, EcoRI and BamHI, or EcoRI and Hind III and the small DNA fragment(s) replaced with the 2.7 Kbp Nde I-EcoRI fragment of pPFg1, the 400 bp EcoRI-BamHI fragment of pPFc1028 or 2.4 Kbp EcoRI-Hind III (where the Hind III site is in the polylinker of the plasmid) fragment of pPFc1028, respectively. In addition, specific fragments such as the 1.2 Kbp EcoRI-Nde I fragment of pPFc1028 can be subcloned into the polylinker region of pUC9 (in this instance as an EcoRI/blunt and fragment), then cut out with EcoRI and Hind III and cloned into pWRL507 cut with EcoRI and Hind III.

By using suitable restriction enzyme sites, DNA fragments from the P.195 gene sequence may be cloned into a site within the trpE gene in the correct orientation, but usually in the wrong translational frame. In order to obtain expression of the inserted sequence, a synthetic linker of suitable length can be inserted into the restriction site between the trpE gene and the insert, to give in-frame expression of the fusion protein. Alternatively the plasmid containing the inserted DNA can be opened at the unique restriction site between the bacterial an the inserted DNA and the DNA treated briefly with the enzyme Bal 31 to remove a few bases from each end of the linearised DNA. After repair with the large (Klenow) fragment of DNA polymerase 1, the plasmid is recircularised with T4 ligase and used to transform bacteria. One in three of the transformants should contain the P.195 sequence in the correct reading frame to be expressed as a fusion protein with the trpE gene product. It will be appreciated by those skilled in the art that the extent of digestion with Bal 31 will determine the final size of the expressed fusion protein and the relative lengths of trpE and P.195 sequences contained within it. In addition, the insertion of a synthetic linker during ligation after Bal 31 digestion and repair facilitates the analysis of particular strains after transformation. By the judicious use of specific restriction enzyme digestion and Bal 31 enzyme treatment, any specific region of P.195 can be expressed as a fusion protein.

Thus, in another feature of the invention is provided a vector, containing a DNA sequence according to the invention tandemly linked to an amino-terminal coding portion of a gene translatable by the relevant host and, optionally, any control sequence(s) associated therewith, which, when used to transform a suitable host will result in production of a fusion protein comprising at least a part of P.195 or a peptide comprising at least one epitope thereof.

An alternative method for expressing DNA fragments is to use an open reading frame (ORF) vector into which (usually)short pieces of DNA can be inserted, often within the sequence coding for the N-terminal amino acid sequence of an *E. coli* protein. The inserted DNA must contain no stop codons in the correct translational frame, be in the correct orientation relative to the direction of transcription, and be in the correct frame at each end. For pieces of DNA from a protein coding sequence generated by a random cleavage method the theoretical probability of read-through in the correct frame is 1 in 18. ORF vectors based on β-galactosidase have been described (Koenen et al., 1982). Insertion of a piece of DNA into a site at the N-terminus of the protein in the correct frame confers read-through expression of the β galactosidase protein which can be detected by the hydrolysis of the chromogenic substrate 5-bromo-4-chloro-3-indolyl-β-D-galactoside (Xgal). For example if Xgal is included in the agar upon which the colonies are grown, transformation of a suitable host strain with a plasmid expressing a functional β-galactosidase will produce a blue colony. One such vector, pXY460, contains the β-galactosidase gene under the control of the tac promoter. Insertion of DNA into the Sma I site next to the EcoRI site may convert the gene to in-frame expression. Transformation of an *E. coli* host such as JM105 converts the bacteria to ampicillin resistance and expression of the fusion protein can be induced at high levels by the addition of isopropyl-β-D-thiogalactopyranoside (IPTG).

Thus, in an alternative aspect of the invention, we provide a vector comprising a gene capable of translation in a suitable host, optionally provided with relevant control sequences, into which is inserted a DNA sequence according to the invention suitably altered such that the portion of said gene carboxy-terminal to said DNA sequence is correctly translated on expression in a suitable host to produce a fusion protein comprising at least a part of P.195 or a peptide comprising at least one epitope thereof and part of said gene-encoded protein.

The peptide coded by part of the P.195 gene in a fusion protein may be cleaved from that fusion protein by enzymic or chemical cleavage of the appropriate peptide bond. It will be apparent to those skilled in the art which enzymic or chemical cleavage method should be employed, by examination of the amino acid sequence expressed. By insertion of a synthetic oligonucleotide linker between the P.195 DNA sequence and the bacterial gene sequence in the fusion protein expression system, a suitable site may be provided for enzymic or chemical cleavage between the P.195 sequence and the remainder of the expressed fusion protein. In this way the P.195 gene-encoded fragments may be purified away from host peptides.

Direct expression of the coding sequence for the P.195 protein or parts thereof can be achieved by placing the inserted DNA sequence directly after an AUG start codon in the correct reading frame such that the DNA insert replaces the coding sequence normally transcribed and translated by the bacterial control region. Such a control region includes a promoter and a ribosome binding site in the optimal position relative to the start codon. The DNA sequence to be expressed may be correctly positioned by the use of suitable restriction sites and if necessary by using a suitable synthetic oligonucleotide linker. At the end of the inserted DNA sequence a stop codon may be inserted in the correct reading frame to stop translation and a terminator sequence to stop transcription may be added. The inserted DNA to be expressed may be the entire coding sequence of P.195 or the entire sequence from which the amino-terminal signal sequence has been removed, or preferably a part of the coding sequence corresponding to an immunogenic fragment of the protein. Suitable fragments may be prepared by restriction enzyme digestion of a suitable cDNA or genomic DNA clone (after examination of the nucleotide sequence), and if necessary further treatment at either or both ends with Bal 31 to digest away in a controlled way parts of the DNA sequence. Controlled digestion is achieved by the selection of proper buffer, temperature, reaction time and amount of enzyme, for example as described in Example 8. At this stage a suitable synthetic linker may be added, preferably by blunt end ligation to the insert, to provide an AUG start codon or facilitate ligation into the expression vector.

According to a further feature of the present invention we provide a method which comprises transforming a host cell with the above-defined cloning vector and culturing the host cell to provide expression of the said P.195, or a peptide comprising at least one epitope thereof.

Controlled expression of any cloned fragment will be possible by use of the sequences at either end of the sequence, or by use of other sequences already known. Such sequences include promoters and enhancers. Examples of such promoters include lac, trp, bacteriophage λ pL and hybrid trp-lac(tac). Suitable enhancers include the SV40 enhancer and the enhancer from bovine papillomavirus.

According to a further feature of the present invention we provide a vector containing the above-mentioned DNA sequence according to the present invention.

The vector referred to above may be any appropriate vector which is suitable for the cloning of the DNA and which may be used to transform a host cell and thereby express the relevant protein. Such vectors include plasmids, bacteriophages and cosmids. Vectors which may be used for cloning cDNA include pUC8, pUC9, pAT153, pBR325 and pBR328 for use in *Escherischia coli*, pBD9 and pKT438 for use in *Bacillus subtilis*, pMA56 for use in yeast and pAdD26SV(A)-3, pSV2-dhfr, SVEHA3 and SVLHA8 for use in mammalian cells.

Vectors for use in expression of the relevant protein will include control sequences, such as mentioned above. Such vectors include pXY460 and pWRL 507 for use in *E. coli* or pSV2-dhfr for use in mammalian cells.

In a further aspect of the invention, we provide a vector containing the DNA sequence according to the invention, further containing one or more control sequences to regulate the expression of said DNA sequence.

Examples of suitable host cells for use in the above-described method may be prokaryotic, such as bacteria (for example *E. coli* HB101 and DH1, *B. subtilis* sp.BD170 and IH6140), or eukaryotic, such as yeast (for example XV610-8C yeast cells) or mammalian cells (for example simian CV-1 cells).

In an alternative embodiment of the invention we provide a method for synthesising at least a portion of P.195 or a peptide comprising at least one epitope thereof, said P.195 or peptide being optionally covalently linked to further peptide sequence, which method comprises the steps of:

a) creating a cDNA or genomic DNA library from *Plasmodium falciparum*;

b) selecting a probe for P.195 and rendering the said probe radio-active;

c) selecting a member or members of the said library by use of the said probe; and d) using DNA thus selected from the said library to transform a suitable host which may be used to express the said P.195 or a peptide comprising at least one epitope thereof.

The present invention further includes the said P.195 protein or peptides comprising at least one epitope thereof, when obtained by any of the above methods according to the invention. These materials may be incorporated into a vaccine for conferring immunity against malaria. For this purpose the antigenic protein or a peptide comprising at least one epitope thereof may be presented in association with a pharmaceutically acceptable carrier. The antigenic proteins or peptides may be used singly or in combination with other P.195 epitope-containing peptides or with other proteins which will provide immunity against malaria.

In a further aspect there is provided a vaccine for inducing immunity to malaria which comprises P.195 or a peptide comprising at least one epitope thereof, in association with a pharmaceutically acceptable carrier.

Pharmaceutically acceptable carriers, in this instance, are liquid media suitable for use as vehicles to introduce the antigen into the patient. An example of such a carrier is saline solution. The P.195 or peptide may be in solution or suspended as a solid in the carrier, or it may be solubilised by the addition of pharmaceutically acceptable detergent.

The vaccine may also comprise an adjuvant for stimulating the immune response and thereby enhancing the effect of the vaccine. A convenient adjuvant for use in the present invention is aluminium hydroxide.

Conveniently the vaccines are formulated to contain a final concentration of P.195 or peptide in the range of from 0.3 to 5 mg/ml, preferably 0.5 to 2 mg/ml, most preferably 1 mg/ml. After formulation the vaccine may be incorporated into a sterile container which is then sealed and stored at a low temperature, for example 4° C., or it may be freeze-dried.

In order to induce immunity in vertebrate hosts to malaria one or more doses of the vaccine suitably formulated may be administered. It is recommended that each dose is 0.1 to 2 ml preferably 0.2 to 1 ml, most preferably 0.5 ml of vaccine.

There is in a further aspect provided a method for inducing immunity to malaria in susceptible vertebrate hosts, comprising the administration of an effective amount of a vaccine, as hereinbefore defined, to the host.

The vaccines may be administered by any conventional method for the administration of vaccines including oral and parenteral (eg. subcutaneous or intramuscular) injection. The treatment may consist of a single dose of vaccine or a plurality of doses over a period of time.

The following examples are for illustration only and are not intended to limit the invention in any way.

EXAMPLE 1

Identification of a cDNA Clone from the P.195 Gene

*P. falciparum* cultures were maintained and synchronized as described by Holder and Freeman (1982 supra) and cells collected by centrifugation 30–40 h. After the last cycle of reinvasion. After washing in PBS (150 mM NaCl, 5 mm KCl and 10 mM sodium phosphate pH7.2) the cells were resuspended in four volumes of 50 mM sodium acetate pH5.5, 100 mM NaCl, 1 mM EDTA and SDS added to 3% w/v. Vigorous extraction with phenol-chloroform (1:1) equilibrated with the same buffer was performed for 5 minutes followed by centrifugation at 16,000 g for 3 minutes. After a second extraction of the aqueous phase, nucleic acids were precipitated with ethanol, centrifuged, the pellet dissolved in 4 ml 0.1M EDTA pH 7.5 and 4 g CsCl added. The RNA was pelleted through a cushion of 95% (w/v) CsCl in 0.1M EDTA by centrifugation at 150,000 g for 16 hours at 25° C., redissolved in distilled water and precipitated twice with ethanol.

To purify the mRNA, oligo-dT cellulose chromatography was performed by standard methods (Maniatis, T., Fritsch, E. F. and Sambrook, J. (1982), molecular cloning, a laboratory manual. Cold Spring Harbor Laboratory, New York). Size fractionation of RNA in sucrose gradients was as described previously (Odink, K. G. et al., J. Biol. Chem. (1981) 256, 1453–1458). A cDNA library was constructed using standard procedures (Maniatis et al., (1982) supra). cDNA was synthesized in a 50 µl reaction containing 6 µg Poly A+ RNA, 5 µg oligo-dT$_{(12-18)}$, 1 mM of each nucleoside triphosphate, 0.1M Tris-HCl pH 8.3, 10 mM MgCl$_2$, 140 mM KCl, 10 mM DTT and 30 U of AMV reverse transcriptase for 90 min at 42° C.

Second strand synthesis was in 0.1 ml 0.1M HEPES pH6.9, 10 mM MgCl$_2$, 2.5 mM DTT, 70 mM KCl, 0.5 mM of each nucleoside triphosphate and 50 U of *E. coli* DNA polymerase large fragment for 16 hours at 15° C. After S1 nuclease digestion, 5 µg of DNA were recovered and 0.5 µg inserted into the Pst I site of pUC8 (Vieira J. and Messing, J. Gene 19, 259–268 [1982]) by homopolymeric G-C tailing. *E. coli* HB101 was used for transformation. Replica filters carrying 3,000 recombinants were probed with $\gamma$-$^{32}$P-ATP polynucleotide kinase-labelled 33S mRNA previously shown by in vitro translation to be enriched for mRNA encoding P.195 (Odink et al, 1984). 60 recombinant plasmids were detected with the probe and 12 of these gave a strong signal. On the basis of cross-hybridization of nick-translated inserts, 6 sub-groups were formed from the 12 recombinants. On the premise that these recombinant probes represented parts of the DNA sequence for P.195, they should hybridize to a mRNA of not less than 5,300 bases long from a total extract of *P. falciparum* mRNA, this being the minimum estimated length necessary to code for a protein of about 195,000 MW. One member of each group was labelled by nick-translation and used as a probe on *P. falciparum* RNA Northern blots. (Thomas, P. S. (1980) Proc. Nat. Acad. Sci. U.S.A. 77, 5201–5). Three recombinants, pFC15, pFC16 and pFC17 with cDNA inserts of 1.6 kb, 2.3 kb and 1.1 kb respectively, hybridized to mRNAs of 9 kb, 7.5 kb and 5.5 kb in size respectively. Isolated insert DNA from pFC17 was treated with exonuclease Bal31 to give randomized reading frames and inserted into an expression plasmid carrying part of the tryptophan operon. DNA was inserted into the Bssh II Site, 13 amino acids from the carboxy terminus of the mature trpE-gene product, anthranilate synthetase I. In-phase insertion of cDNA into this site gives a fusion protein carrying 56,000 MW of anthranilate synthetase I. Upon induction of the gene, by tryptophan starvation in the presence of β-indole acrylic acid, one of the resulting recombinants, pFT 1733, gave a fusion protein of 72,000 MW (as determined by SDS-PAGE) representing an additional 16,000 MW encoded by the cDNA insert.

Bacterial extracts and an extract of *P. falciparum* schizonts were subjected to SDS polyacrylamide gel electrophoresis, transferred to nitrocellulose and then probed with a polyvalent rabbit serum specific for P.195. The fusion protein of pFT1733 was clearly detected by the antiserum. The antiserum was highly specific for P.195 as, from a total *P. falciparum* schizont extract, only P.195 was detected. There was no reaction with a bacterial extract containing an 80,000 MW fusion protein consisting of the trpE gene product and a foot and mouth disease virus VP1 protein. In addition, the control using normal rabbit serum showed no binding. Thus, pFC17 encodes some of the antigenic determinants of *P. falciparum* P.195. Further reference to pFC17 will be by its synonym, pPFc1017.

EXAMPLE 2

Preparation of Further Overlapping cDNA Clones Related to pPFc1017

A recombinant cDNA library was constructed from size fractionated cDNA. cDNA, prepared and tailed as described in Example 1, was centrifuged through a 5 ml 5% to 20% (w/v) sucrose gradient in 25 mM Tris HCl pH 7.4, 100 mM NaCl, 2.5 mM EDTA for 3.5 hrs to 45,000 rpm in an SW50.1 rotor (Beckman Instruments). cDNA in the 2 kbp to 8 kbp region (about 100 ng) was harvested, annealed with 300 ng dG-tailed Pst 1 digested pUC9 and used to transform DH1 cells to ampicillin resistance. 1200 recombinants were obtained on 6 agar plates. Replica filters were probed with the insert DNA from pPFc1017 which had been labelled by nick translation. Eleven clones were indentified as containing DNA hybridising to this probe. These clones were numbered pPFc1001 to 1011. This library was subsequently rescreened using a part of the insert in pPFc1007 which did not cross-hybridise with pPFc1017. A further 8 clones, pPFc1028 to 1035, were isolated which hybridised to this probe.

Plasmid DNA from these cDNA clones was purified by centrifugation on caesium chloride gradients and characterized by restriction enzyme mapping and cross-hybridisation. The cDNA clones were aligned in an overlapping linear sequence. The positions of the six cDNA clones used in the sequence analysis are shown in FIG. 2.

EXAMPLE 3

Isolation of Genomic Clone pPFg1 from the P.195 gene

100 µg *P. falciparum* DNA (prepared according to the method of Odink et al., (1984) supra) was digested to completion with Hind III, the sample loaded on a 10–40% sucrose gradient containing 1M NaCl, 20 mM Tris. HCl, pH 8.0, 5 mM EDTA and centrifuged in a Beckman SW27 rotor for 24 hrs at 26,000 rpm, 20° C. 0.5 ms fractions were collected by bottom puncture of the tube and aliquots of alternate fractions were run on a 1% agarose gel. Fractions in the region of the gradient giving a positive signal on dot blot hybridization with nick-translated pPFc1017 were digested with EcoRI and ligated with gel-purified Hind III+EcoRI cleaved pUC8 DNA. About 40 transformants in DH1 from each fraction were screened on nitrocellulose filters by colony hybridisation with pPFc1017 insert (Grunstein, M. and Hogness, D., Proc. Natl. Acad. Sci. 72, 3961 (1975)). One colony from fraction 39 gave a positive signal. This recombinant, pPFg1, contains a 3.1 kb Hind III-EcoRI fragment which co-migrates with the corresponding genomic DNA fragment, and both have the same restriction enzyme maps. A restriction map of pPFg1 was obtained by partial end-label mapping of pPFg1 insert (Smith, H. O. and Birnstiel, M. L., Nucl. Acid Res., 2387 (1976)). Sequencing was performed by the Sanger dideoxy method described in Example 5.

EXAMPLE 4

Construction of a Map of the P.195 Gene in *P. falciparum* DNA

*P. falciparum* DNA was prepared as described (Odink et al., (1984) supra) and aliquots of it were restricted with specific endonucleases, either individually or on some occasions as a double digest, i.e. with two restriction endonucleases. The products were electrophoresed on agarose gels (0.7% to 1.5%) in Tris-Borate-EDTA (pH 8.2) containing 0.5 µg/ml Ethidium bromide and together with DNA fragments of known length as size markers in parallel tracks. The DNA was transferred to Gene Screen Plus (New England Nuclear/Dupont) by a capillary blot procedure and hybridised to $^{32}$P-labelled probe DNA at 42° C. in the presence of 50% formamide, according to the protocols suggested by the manufacturer. Hybridised probe DNA was detected by autoradiography at −70° C. using X-Omat S film between Cronex Lightning-Plus screens.

The probe DNA was specific plasmid DNA or specific sequences excised from the cDNA or genomic DNA plasmid clones, and purified by agarose gel electrophoresis and elution. The DNA was labelled with $^{32}$P by nick translation with *E. coli* DNA polymerase in the presence of $^{32}$[P] α-ATP. An analysis of the size of restriction fragments from within the genomic DNA hybridising to specific probes enabled a linear map of restriction enzyme sites to be constructed. Such a map of the P.195 gene is shown in FIG. 3 with some exemplary sites and probes to which the specific fragments hybridised. It will be appreciated that several other specific digests of genomic DNA were performed and were probed with other specific fragments from the cloned DNA, and the results were consistent with the map shown in FIG. 3. To improve clarity of the map, not all of the restriction sites present in the DNA sequence are indicated.

An examination of the genomic map and the restriction enzyme map derived from the DNA sequence indicates that these two are colinear in the region corresponding to the coding sequence for the protein, to the right hand size of the Hind III site at nucleotide 313. However, there appears to be an additional 700 bp of sequence in the genomic DNA, not present in the cDNA clones, located between the Mba 1 site and the Hind III sites at nucleotides 221 and 313 in the cDNA sequence. This may represent an intron in the very start of the coding sequence.

The sites shown on the map are some of those for the enzymes A (Alu1), B(Bam H1), E(EcoR1), H(Hind III), M(Mbo1), N(Nde1), P(Pst1), Pv(PvuII), R(Rsa1) and T(Taq1). The probes were either total plasmids or specific fragments derived by digestion with specific enzymes at sites within the insert or within the plasmid polylinker region.

EXAMPLE 5

Nucleotide Sequence of the DNA Coding for P.195

Sequence analysis of the DNA was done using the chemical cleavage method of Maxam and Gilbert (Maxam and Gilbert, 1980, supra) and the dideoxy procedure of Sanger (Sanger et al., 1977, supra).

1. Chemical cleavage

The DNA fragments suitable for sequence analysis were prepared as follows.

a) The DNA was digested with restriction endonuclease (under the conditions described by the suppliers), then calf intestine alkaline phosphatase (Boehringer Mannheim) was added to the mixture and the reaction continued for 30 min. at 37° C. The DNA was extracted with chloropane and ethanol precipitated. The 5' ends of the DNA were labelled with [$^{32}$P] using polynucleotide kinase as described by Maniatis (Maniatis et al., 1982, supra). The labelled DNA was cut with a second suitable restriction endonuclease and the mixture was loaded into 1% (w/v) agarose gel, the DNA bands of interest were electro-eluted from this agarose gel and their sequences were determined.

b) Fragments of DNA were also prepared by modification of the procedure described in section a). The DNA was digested with restriction endonuclease, phosphatased and labelled at the 5' end with [$^{32}$P] as outlined above. The DNA fragments were then denatured by addition of de-ionized formamide (final concentration 70% (v/v)), and heated to 100° C. for 5 minutes. The samples were quickly cooled in iced water and immediately loaded onto a non-denaturing 15% polyacrylamide gel (with acrylamide to bis-acrylamide ratio of 60:1 (w/w)). The separated DNA strands were electro-eluted from the gel and sequenced.

2. Dideoxy sequencing

The DNA templates were prepared by subcloning fragments of the insert in the filamentous phage cloning/sequencing vector M13mp8 (Messing and Vieira, 1982, supra). The sequencing was performed using a synthetic universal primer (Celltech) and [$^{35}$S]-d ATPαS (Amersham International) as described by Sanger et al., 1977, supra. Two basic strategies were used to sequence specific fragments. In the first, specific restriction fragments (produced by digestion with RsaI, HinfI-Aha III, Taq1) were purified by electro-elution, and where necessary, the staggered ends made blunt using the Klenow DNA polymerase I fragment. Fragments difficult to clone or sequence by the above protocol were treated with Bal-31 (Maniatis et al., 1982). Conditions (DNA and enzyme concentration) were chosen such that 100–150 bp DNA was removed from each end of the fragment in 1 minute at 30° C. By digesting over a time course a series of overlapping fragments were obtained. Bal-31 treated DNA was repaired with DNA polymerase I Klenow fragment. DNA was ligated with phosphatase-treated SmaI-digested M13mp8 (Amersham) and transfected intoJM103 or JM101 (Messing, J., et al., Nucl. Acid Res. 9, 309 (1981)). Template DNA was prepared according to standard procedures. Wherever possible, sequence was obtained from both strands of each clone.

The total sequence obtained by overlapping the sequences of the individual clones is shown in FIG. 1. The clones used to determine the sequence are shown beneath the restriction map obtained from the DNA sequence in FIG. 2.

EXAMPLE 6

Purification of the 83,000 MW Fragment from Culture Supernatants and the Determination of a Partial Amino Acid Sequence Supernatants from in vitro cultured *P. falciparum* (described in Example 1) were harvested and centrifuged at 10,000 g for 5 minutes to remove cellular debris. To each 100 ml culture supernatant was added 1 ml 1M Tris, 100 mM EDTA, 100 mM EGTA, 1 ml 100 mM PMSF, 1 ml 0.5M iodoacetamide, 1 ml 10 mM TLCK and 0.5 g sodium deoxycholate. The pH was adjusted to 8.2 with HCl and then the sample was centrifuged at 100,000 g for 45 minutes. The supernatant after centrifugation was then applied to a 10 ml column of antibody 89.1-Sepharose (prepared as described by Holder and Freeman, 1984b supra) which had been pre-equilibrated with 10 mM Tris-HCl pH 8.2 containing 1 mM EDTA; 1 mM EGTA and 0.5% (w/v) sodium deoxycholate (equilibration buffer). After the column had been washed extensively with equilibration buffer, material retained on the column was eluted with 50 mM diethylamine HCl, pH 11.5, containing 0.5% (w/v) sodium deoxycholate. The eluate was concentrated by ultrafiltration using an Amicon XM50 filter and adjusted to pH 8.2. The major polypeptide in the eluate was the 83,000 MW species, and it was the only component which reacted with either monoclonal antibody 89.1, rabbit polyvalent anti-P.195 serum or human *P. falciparum* immune serum, on Western blots. The major contaminant in the preparation was IgG which was removed from the concentrated eluate by passage through a Protein A-Sepharose column (0.9×10 cm) (Pharmacia Fine Chemicals) equilibrated as described above. The unretarded material, depleted of IgG, was collected. Solid guanidinium chloride was added until a clear solution was obtained and then the protein was reduced and S-carboxymethylated (Waxdal M. J. et al., Biochemistry 7 1959–1966 (1968)). The reduced and S-carboxymethylated 83,000 MW polypeptide was finally purified by passage through a column of Sephacryl S300 (Pharmacia Fine Chemicals, Sweden) equilibrated with 10 mM Tris HCl pH 8.2, containing 1 mM EDTA, 1 mM EGTA and 6M guanidinium chloride. Fractions were assayed spectrophotometrically at 280 nm and by SDS-PAGE analysis of aliquots, and those containing the 83,000 MW species were pooled. After extensive dialysis against water and 5% (v/v) formic acid the sample was freeze-dried, prior to application to the automatic sequencer in a small volume of 5% formic acid. The protein was subjected to 20 cycles of automated Edman degradation in a Beckman 890C sequencer equipped with a Sequamat P6 autoconverter and a Sequamat SC-510 program controller using a 0.33M Quadrol program, as described by Baccanari D. P. et al., J. Biol. Chem. 259, 12291–12298 (1984). The released phenylthiohydantoin derivatives of amino acids were identified by reverse-phase HPLC and confirmed by back hydrolysis (Baccanari et al., 1984 supra). Starting from 910 ml of culture supernatant, 5.9 mg of protein was present in the eluate from the affinity column, 2.6 mg of protein passed through the protein A-Sepharose column and 400 µg of purified protein was subjected to the Edman degradation.

The following partial amino acid sequence was obtained from the successive cycles of degradation starting at the N-terminal amino acid of the polypeptide.

| 1. | 2. | 3. | 4. | 5. | 6. | 7. | 8. | 9. | 10. |
|---|---|---|---|---|---|---|---|---|---|
| N.I. | N.I. | N.I. | N.I. | N.I. | Tyr | Gln | Glu | Leu | Val |
| 11. | 12. | 13. | 14. | 15. | 16. | 17. | 18. | 19. | 20. |
| Lys/Phe | Lys/Phe | Leu | Glu | Ala | Leu | Glu | Asp | Ala | Val |

The residues at positions 1 to 5 were not clearly identified (N.I.) and lysine and phenylalanine derivatives were not separated from each other in the HPLC system employed.

By examination of the nucleotide sequence derived from the cDNA and genomic DNA clones it can be seen that this sequence of residues (6 to 20) corresponds to the translated sequence of nucleotides 288 to 332.

On this analysis the 83,000 MW fragment is derived from the amino terminal sequence of the P.195 precursor. In the complete sequence the AUG (Methionine) start codon at nucleotide 216 is followed by nucleotide sequence of 18 amino acids which may correspond to a signal sequence present on the primary translation product for many membrane or secreted proteins, and which is normally cleaved of during the passage of the protein into the lumen of the endoplasmic reticulum (Kreil, G., Ann. Rev. Biochem. 50, 317–348 (1981)).

EXAMPLE 7

The Reaction of Antibodies with Processing Fragments of P.195 and the Position of these Fragments within the Linear Coding Sequence By direct amino acid sequencing, the amino-terminus of the 83,000 MW fragment has been located close to the amino terminus of P.195 (Example 6). The other fragments produced by in vivo proteolytic processing can be located in the linear gene sequence by an analysis of the sizes of polypeptides recognised by specific antibodies (preferably monoclonal antibodies) raised against P.195. Two monoclonal antibodies were used in this analysis. Antibody 89.1 (Holder and Freeman, 1982, supra) reacts with intracellular P.195 in schizonts and with the 83,000 MW fragment on the merozoite surface. It does not react (by immunofluorescence) with the subsequent ring stage of the parasite, consistent with the loss of this fragment during merozoite invasion of red cells. Antibody 111.2 reacts with intracellular P.195 in schizonts, with the merozoite surface and with the ring stage parasite by immunofluorescence. This specificity is similar to that of a monoclonal antibody described recently by Hall et al. (1984a, supra).

P.195 and processing fragments of it can be labelled in vitro by the addition of [$^{35}$S] methionine to cultures of the parasite in methionine-free medium (Holder and Freeman, 1982, supra, Freeman and Holder, 1983, supra). The processing fragments on the surface of naturally released merozoites can be labelled by radio-iodination with [$^{125}$I] iodine using lactoperoxidase as described (Freeman and Holder, 1983b supra; Holder and Freeman 1984b, supra).

From detergent extracts of [$^{35}$S] methionine-labelled schizonts a rabbit polyvalent antiserum against P.195 immunoprecipitated P.195 and fragments which have molecular weights of 153,000; 110,000; 83,000; 45,000; 42,000 and 29,000 as determined by SDS-PAGE analysis. On non-reducing gels (in the absence of dithiothreitol) the 45,000 and 42,000 MW species migrated with apparent molecular weights of 38,000 and 36,000 respectively. Antibody 89.1 immunoprecipitated P.195 and the 153,000, 110,000 and 83,000 MW species. Antibody 111.2 immunoprecipitated P.195 and the 45,000 and 42,000 MW species.

From detergent extracts of surface-labelled merozoites the polyvalent anti-P.195 serum immunoprecipitated three fragments which have apparent molecular weights of 83,000, 42,000 and 19,000. The 83,000 MW fragment was immunoprecipitated by antibody 89.1. Antibody 111.2 immunoprecipitated the 42,000 and 19,000 MW species. An analysis of these fragments by peptide mapping showed that they were probably non-overlapping pieces of P.195 (Holder and Freeman, 1984b supra).

Based on these data and that described in examples 6 and 10 the linear order of the fragments within the P.195 coding sequence can be determined. The amino acid sequence determined for the amino terminus of the 83,000 MW fragment corresponds to the sequence at the 5' end of the coding region of the gene, immediately after the presumptive signal sequence. Therefore the 83,000 MW fragment is derived from the amino terminal 42% of P.195. The major intermediate processing fragment of 153,000 MW which is recognised by antibody 89.1 and not by antibody 111.2 is derived from the amino terminal 78.5% of the coding sequence, and therefore including all of the 83,000 MW fragment. The 42,000 MW fragment is derived from the carboxy-terminal 21,5% of the coding sequence, since the antibody 111.2 does not react with the 153,000 MW fragment. The 19,000 MW fragment is presumably located within the sequence of the 153,000 MW species, but not within the 83,000 MW species.

EXAMPLE 8

Expression of P.195 Sequences as Fusion Proteins in *E. coli* and Purification of the Products In separate experiments, pWRL507 (FIG. 4 of the accompanying drawings) was digested with Nde1 and EcoR1, EcoR1 and BamH1 or EcoR1 and Hind III and the relevant fragments purified by agarose gel electrophoresis. This DNA (0.1 pmoles) was ligated with 0.5 pmoles of the DNA fragments derived from the P.195 recombinants by the relevant pairs of restriction enzymes and then used to transform DH1 cells to ampicillin resistance. Colonies were screened by restriction enzyme digests of small plasmid preparations. Strains with plasmid containing the insert were further grown in M9 minimal medium containing 100 µg/ml ampicillin and 10 µg/ml indole acrylic acid (induced expression) or 100 µg/ml ampicillin and 10 µg/ml tryptophan (non-induced). Bacteria were harvested by centrifugation at 10,000 g for 1 minute and then lysed by the addition of SDS sample loading buffer for PAGE (62.5 mM Tris-HCl pH 6.8 containing 2% (w/v) sodium dodecyl sulphate, 10% (v/v) glycerol, 0.1M dithiothreitol and 0.005% (w/v) bromophenol blue). Aliquots were subjected to analysis by SDS-PAGE and then the gels were stained with coomassie blue to detect total protein or the resolved proteins were transferred to nitrocellulose and used for Western blotting with a polyvalent antiserum raised against purified P.195. A strain containing the Nde I-EcoR1 fragment of pPFg1 produced an inducible fusion protein of 135,000 MW which could be detected in lysates by coomassie blue staining and by reaction with the polyvalent antiserum. This corresponds to a fusion protein containing 233 amino acids from the N-terminus of the trpE gene product and 907 amino acids from P.195. A strain containing the EcoRI-BamH1 fragment of pPFc1028 produced a fusion protein of 53000 molecular weight containing 326 amino acids from trpE and linker and 156 amino acids from P.195. A strain containing the EcoRI-Hind III fragment of pPFc1028 produced a fusion protein of 105,000 MW consisting of 326 amino acids from trpE and linker and 594 amino acids from P.195. A strain containing the EcoRI-Nde I fragment from pPFc1028 produced a fusion protein of 85,000 MW consisting of 326 amino acids from trpE and 401 amino acids from P.195. In each case the fusion protein was detected by coomassie blue staining and reacted with the polyvalent anti-P.195 serum on Western blots.

A 750 bp Rsa I Hind III fragment derived from the cDNA clone pPFc1013, comprising nucleotides 863 to 1613 together with a G-C tail and part of the pUC9 polylinker region from the Pst I site to the Hind III site was sub-cloned into the plasmid pUC9 which had been cut with Hind II, treated with calf intestinal phosphatase and further digested with Hind III. The insert was subsequently cut out of pUC9 using EcoRI and Hind III and inserted (in the correct orientation) into pWRL507 cut with EcoRI and Hind III. To obtain in-frame expression, 5 µg of the plasmid was treated with EcoRI restriction enzyme to linearise the construct. The DNA was precipitated with ethanol, re-dissolved in 50 µl H$_2$O containing 50 µg/ml BSA and then mixed with an equal volume of Bal 31 buffer (Maniatis et al., (1982) supra). The DNA was digested with 0.02 units of enzyme Bal 31 (Biolabs) for 1 minute at 30° C. and then the reaction was terminated by the addition of 20 µl 1M Tris 100 mM EDTA 100 mM EGTA. The DNA was purified by agarose gel electrophoresis, and then treated with DNA polymerase 1 large fragment (Klenow) in the presence of nucleotide triphosphates using 2.5 units of enzyme (Boehringer/Mannheim) in a final volume of 50 µl nick translation buffer (Maniatis et al., (1982) supra) for 90 minutes at room temperature. The DNA (0.1 pmole) was then recircularised by incubation overnight with 200 units T4 DNA ligase (Biolabs) at 7° C., and then used to transform DH1 cells to ampicillin resistance. Ten individual transformed strains were screened by restriction enzyme analysis of the plasmid DNA. One group of 8 transformants contained plasmids which had lost the EcoRI site. This group was further analysed by growth in M9 medium in the presence of indole acrylic acid or tryptophan. One strain produced a fusion protein of approximately 65,000 MW when grown in the presence of indole acrylic acid, and this fusion protein reacted with polyvalent anti-P.195 serum on a Western blot.

In a similar manner the Nde I-Hind III fragment from pPFc1028 (where the Hind III site is the plasmid polylinker) was first subcloned as a blunt end-Hind III fragment into pUC9 that had been cut with Hind II and Hind III. After inserting this fragment into pWRL507 cut with EcoRI and Hind III, the new construct was reopened with EcoRI, treated with Bal 31 and then recircularised as described above. One strain produced a fusion protein of approximately 56,000 MW which was detected on Western blots with anti-P.195 serum, and containing the C-terminal 190 amino acid sequence of the coding region for the P.195 gene.

Relatively pure preparations of the individual fusion protein were produced from cell lysates. A single colony from a strain was grown up overnight at 37° C. in 100 ml M9 medium containing 50 μg/ml ampicillin. The following day the overnight culture was diluted with 400 ml M9 culture medium containing 50 μg/ml ampicillin and 10 μg/ml indole acrylic acid and incubated for 5 hrs at 37° C. The bacteria were harvested by centrifugation at 6000 g for 10 minutes. The bacterial pellet was suspended in 10 ml 25 mM Tris pH 8.0 containing 1 mM EDTA, 1 mM PMSF, 0.2% (v/v) NP40 and 1 mg/ml lysozyme and left on ice for 2 hrs. After this time 20 μl of 1M MgSO$_4$ and 200 μl of 1 mg/ml DNAse were added and the sample was left to incubate for a further 2 hrs on ice. The insoluble material was harvested by centrifugation at 20,000 g for 10 minutes and the supernatant (S1) was retained. The pelleted material was washed by suspension in 10 ml 50 mM Tris-HCl pH 8.0 containing 5 mM EGTA, 5 mM EDTA, 1 mM PMSF and 1% NP40. The material was centrifuged at 20,000 g for 10 minutes and the supernatant was retained (S2). The pellet was resuspended in 10 ml 50 mM Tris HCl pH 8.1, 5 mM EGTA, 5 mM EDTA, 0.5M KSCN, and then centrifuged at 20,000 g for 10 min to yield a third supernatant (S3) and a pellet fraction (P). The pellet fraction was resuspended in 10 ml H$_2$O with and without the addition of 0.1% (w/v) sodium dodecyl sulphate, to solubilise the material and then dialysed extensively against 0.89% NaCl. Aliquots of each supernatant and pellet fraction were analysed by SDS-PAGE and coomassie blue staining and by Western blotting. In instances where there was a high level of expression of fusion protein, this procedure resulted in a final pellet fraction that contained predominantly the fusion protein and therefore constituted an effective purification of the fusion protein. In instances where the level of expression was lower, the fusion protein was present in both S1 and P fractions.

Two Dde 1 Fragments from pPFc1028 corresponding to nucleotides 2961 to 4754 (1793 nucleotides) and nucleotides 4753 to 5128 (375 nucleotides) were purified by agarose gel electrophoresis, treated with 0.04 units of Bal 31 nuclease at 30° C. for 2.5 minutes and then repaired with the Klenow Fragment of DNA polymerase I as described above. The DNA was ligated into PXY460 which had been cut with Sma 1 and treated with calf alkaline phosphatase and this was then used to transform JM105 cells to ampicillin resistance. Transformants were plated onto Agar plates containing Xgal and resultant blue colonies were picked. Strains obtained in this way were screened by restriction enzyme analysis of the plasmid DNA, coomassie blue staining and Western blotting of lysates from cells grown in the presence of IPTG. Strains containing the large Dde1 fragment all produced a large fusion protein which reacted with the rabbit polyvalent anti-P.195 serum. 10 strains containing the smaller Dde1 fragment were investigated as described but only one appeared to produce a fusion protein which was significantly larger than wild type β-galactosides and this fusion protein reacted with the rabbit anti-P.195 serum. Although the remaining strains contained the insert the gene product was the same size as the normal β-galactosidase and did not react with the rabbit anti-P.195 serum. The one strain that produced a fusion protein contained an insert of 310 bp which covers the C-terminal region of the protein.

EXAMPLE 9

Direct Expression of P.195 Sequences in *E. coli*

The EcoRI-Nde I and EcoRI-Hind III fragments derived from pPFc1028 were inserted into pWRL507 as described in Example 8, and were expressed directly by replacing the Pst I-EcoRI fragment in the trpE expression plasmid by the Pst I-EcoRI fragment from pXY460 (FIG. 4). In this construction the trp control region and coding sequence are replaced by the Tac control region (de Boer, H. A. et al., Proc. Natl. Acad. Sci 80, 21–25 (1983)) and an AUG start codon. Directly expressed products were detected in cell lysates by Western blotting with antisera raised against purified P.195. The direct expression products from these two constructions had apparent molecular weights of 47,000 and 70,000 respectively.

EXAMPLE 10

Analysis of the Immunogenicity and Antigenicity of the Fusion Proteins Produced in *E. coli*

A rabbit polyvalent antiserum specific for the *P. falciparum* derived P.195 was obtained by immunising a rabbit with 100 μg of the protein in Freund's Complete Adjuvant (FCA, Difco Laboratories, Detroit) and then boosted with 100 μg of the protein in Freund's incomplete adjuvant (FIA) on days 22, 43 and 211. On day 218 after the primary immunisation the serum was collected.

Polyvalent antiserum was produced by immunization with the purified fusion proteins (Example 8). Rabbits were immunized subcutaneously with 250 μg of the protein in FCA and then boosted with 50 μg of the protein in FIA on day 21. On day 35 after the primary immunization serum samples were collected. Mice were immunized intraperitoneally with 125 μg of the protein in FCA and boosted with the same dose on day 23. On day 30 after the primary immunisation serum samples were collected.

The titration of an antiserum for the binding of antibodies to a protein can be quantified by a solid phase radioimmunoassay (RIA) in which the wells of a microtitre plate were coated with the protein and then serial dilutions of the antibody solution are added to the series of wells. After washing away the unbound antibodies the bound antibodies are detected using a highly labelled specific reagent for the first antibodies, such as protein A from *Staphylococcus aureus* of affinity purified IgG specific for the first antibodies. The proteins which were used to coat the microtitre plates were either the fusion proteins purified from lysates of *E. coli* as described in Example 8, or the P.195 purified by monoclonal antibody affinity chromatography from extracts of *P. falciparum* infected red cells as described by Holder and Freeman (1984b, supra).

The antigens were diluted to 20 μg/ml in 0.05M NaHCO$_3$ pH 9.6 and 50 μl of this solution was added to each well of a 96 well PVC microtitre plate (Dynatech Laboratories). After 90 minutes the plate was washed thoroughly with phosphate-buffered saline supplemented with 0.5% (v/v) Tween 40 and 0.2% (w/v) bovine serum albumin (wash buffer). 50 μl of each serum dilution was added to duplicate wells and after 30 minutes the plate was washed for 10 minutes in wash buffer. Specific antibody was detected by addition of 50 μl of $^{125}$I-labelled protein A ($1.5 \times 10^5$ cpm) for 30 minutes, followed by extensive washing and determination of bound radioactivity using a Packard PED gamma counter.

As can be seen from Table 1 rabbits immunized with the fusion proteins containing P.195 sequences produced antibodies which reacted with the purified P.195 in the RIA and the polyvalent antiserum against P.195 contained antibodies which reacted with the fusion proteins. In this instance, fusion protein 1 is the product of the pPFc1028 EcoRI-Nde1 fragment inserted into trpE and fusion protein 2 is the product of the pPFc1028 EcoRI-Hind III fragment inserted into trpE.

In Example 8 it was shown that the fusion proteins reacted with antibodies in the polyvalent anti-P.195 antiserum on Western blots. The antiserum raised against the fusion proteins reacted with the fusion proteins and with the purified P.195 protein, on Western blots.

The position of the processing fragment sin the linear coding sequence was determined partially by immunoprecipitation from a detergent extract of $^{35}$S-methionine labelled *P. falciparum* (Example 7). When the antisera against the fusion proteins were used to immunoprecipitate proteins from this extract, P.195 was recognised in each case. In addition the rabbit antiserum raised against protein coded by the pPFc1028 EcoRI-Nde1 insert reacted predominantly with the 153,000 and 29,000 MW fragments. The rabbit antiserum raised against the pPFc1028 EcoRI-Hind III insert reacted predominantly with the 42,000 MW fragment.

TABLE 1

Antibody Binding to Different Antigens by Solid Phase RIA
$^{125}$I-Protein A (cpm) bound by antibodies in antisera at F$^1$O dilution

| Antigen | Normal Rabbit | Rabbit anti- P.195 | Rabbit anti- Fusion Protein 1 | Rabbit anti- Fusion Protein 2 |
|---|---|---|---|---|
| P.195 | 161 | 6581 | 1959 | 1432 |
| Fusion Protein 1 | 234 | 2007 | 10952 | 13291 |
| Fusion Protein 2 | 52 | 1093 | 3600 | 3416 |

We claim:

1. An isolated nucleic acid consisting of a sequence encoding the P.195 protein of *P. falciparum* having the amino acid sequence shown in FIGS. 1A–1I.

2. The isolated nucleic acid according to claim 1 having the sequence from nucleotide 216 to 5177 of the nucleic acid sequence of FIGS. 1A–1I.

3. An isolated nucleic acid consisting of the sequence of nucleotides 1–5760 of FIGS. 1A–1I.

4. An isolated nucleic acid consisting of a sequence encoding amino acids 20–1654 of the amino acid sequence shown in FIG. 1A–1I.

5. The isolated nucleic acid according to claim 4 having the sequence from nucleotide 273 to nucleotide 5177 of the nucleic acid sequence shown in FIGS. 1A–1I.

6. An isolated nucleic acid consisting of a sequence encoding a fragment of the P.195 protein having the amino acid sequence shown in FIGS. 1A–1I, wherein said encoded fragment begins at amino acid 20 in FIG. 1A and has a molecular weight of about 83,000 daltons.

7. The isolated nucleic acid according to claim 6, which is a segment of the nucleic acid sequence shown in FIGS. 1A–1I, and said segment begins at nucleotide 273.

8. An isolated nucleic acid consisting of a sequence encoding a fragment of the P.195 protein having the amino acid sequence shown in FIGS. 1A–1I, wherein said encoded fragment begins at amino acid 20 in FIG. 1A and has a molecular weight of about 153,000 daltons.

9. The isolated nucleic acid according to claim 8, which is a segment of the nucleic acid sequence shown in FIGS. 1A–1I, and said segment begins at nucleotide 273.

10. An isolated nucleic acid consisting of a sequence encoding a carboxy terminal fragment of the P.195 protein having the amino acid sequence shown in FIGS. 1A–1I, wherein said encoded carboxy terminal fragment has a molecular weight of about 42,000 daltons.

11. The isolated nucleic acid according to claim 10, which is a segment of the DNA sequence shown in FIGS. 1A–1I, and said segment ends at nucleotide 5177.

12. A recombinant molecule comprising a vector and a nucleic acid sequence selected from the group consisting of the isolated nucleic acids of claims 1, 2, 3, 4, 5, 6, 7, 8, 9, 10, and 11.

13. The recombinant molecule according to claim 12, further comprising a control sequence that is operably linked to said nucleic acid sequence and regulates the expression of said nucleic acid sequence.

14. The recombinant molecule according to claim 13, further comprising a heterologous protein coding sequence tandemly linked amino terminal to said DNA sequence.

15. A host cell comprising the recombinant molecule according to claim 12.

16. A method of producing a polypeptide, comprising culturing a host cell according to claim 15 under conditions such that said DNA sequence is expressed and said encoded peptide is thereby produced, and isolating said polypeptide.

* * * * *